(12) United States Patent
Mizukura et al.

(10) Patent No.: US 11,602,265 B2
(45) Date of Patent: Mar. 14, 2023

(54) CONTROL DEVICE, ENDOSCOPIC IMAGING DEVICE, CONTROL METHOD, PROGRAM, AND ENDOSCOPIC SYSTEM

(71) Applicant: SONY CORPORATION, Tokyo (JP)

(72) Inventors: Takami Mizukura, Kanagawa (JP); Takeshi Uemori, Tokyo (JP); Kentaro Fukazawa, Tokyo (JP); Daisuke Kikuchi, Kanagawa (JP); Tsuneo Hayashi, Tokyo (JP)

(73) Assignee: SONY CORPORATION, Tokyo (JP)

( * ) Notice: Subject to any disclaimer, the term of this patent is extended or adjusted under 35 U.S.C. 154(b) by 855 days.

(21) Appl. No.: 16/078,395

(22) PCT Filed: Jan. 20, 2017

(86) PCT No.: PCT/JP2017/001872
§ 371 (c)(1),
(2) Date: Aug. 21, 2018

(87) PCT Pub. No.: WO2017/168986
PCT Pub. Date: Oct. 5, 2017

(65) Prior Publication Data
US 2019/0069766 A1    Mar. 7, 2019

(30) Foreign Application Priority Data

Mar. 31, 2016 (JP) .............................. JP2016-069872

(51) Int. Cl.
*A61B 1/045* (2006.01)
*A61B 1/00* (2006.01)
(Continued)

(52) U.S. Cl.
CPC .......... *A61B 1/045* (2013.01); *A61B 1/00045* (2013.01); *A61B 1/000095* (2022.02);
(Continued)

(58) Field of Classification Search
None
See application file for complete search history.

(56) References Cited

U.S. PATENT DOCUMENTS

| 4,947,246 A | * | 8/1990 | Kikuchi | ............... H04N 5/2354 348/70 |
| 5,879,284 A | * | 3/1999 | Tsujita | ................... A61B 1/043 600/109 |

(Continued)

FOREIGN PATENT DOCUMENTS

| DE | 102014112666 A1 | * | 3/2016 |
| JP | 57-78834 A | | 5/1982 |

(Continued)

OTHER PUBLICATIONS

International Search Report dated Apr. 4, 2017 in PCT/JP2017/001872, 2 pages.

(Continued)

*Primary Examiner* — John P Leubecker
*Assistant Examiner* — Minqiao Huang
(74) *Attorney, Agent, or Firm* — Xsensus LLP

(57) ABSTRACT

A control device includes an image quality control unit configured to control image quality of an image for display on a basis of optical axis angle information with reference to a scope axis of an endoscope and an image signal acquired by an image sensor. The optical axis angle information is information detected by information obtained by acquiring light source angle information controlled by an imaging device.

15 Claims, 49 Drawing Sheets

(51) Int. Cl.
  *A61B 1/04* (2006.01)
  *G02B 23/24* (2006.01)
  *A61B 1/06* (2006.01)
  *G06T 5/00* (2006.01)

(52) U.S. Cl.
  CPC .......... *A61B 1/00183* (2013.01); *A61B 1/042* (2013.01); *A61B 1/0623* (2013.01); *A61B 1/0669* (2013.01); *G02B 23/24* (2013.01); *G06T 5/003* (2013.01); *G06T 5/006* (2013.01); *G06T 5/009* (2013.01); *G06T 2207/10024* (2013.01); *G06T 2207/10068* (2013.01); *G06T 2207/10152* (2013.01); *G06T 2207/20201* (2013.01); *G06T 2207/30004* (2013.01)

(56) References Cited

U.S. PATENT DOCUMENTS

| | | | |
|---|---|---|---|
| 6,280,378 B1 | 8/2001 | Kazuhiro et al. | |
| 7,106,371 B1* | 9/2006 | Kubo | H04N 5/367 348/246 |
| 2001/0009590 A1* | 7/2001 | Holm | H04N 9/64 382/162 |
| 2003/0187319 A1* | 10/2003 | Kaneko | A61N 2/00 600/9 |
| 2005/0100333 A1 | 5/2005 | Kerschbaumer et al. | |
| 2007/0019887 A1* | 1/2007 | Nestares | G06T 3/4053 382/299 |
| 2009/0147998 A1* | 6/2009 | Yamaguchi | G06T 5/003 382/106 |
| 2010/0265365 A1 | 10/2010 | Oshita | |
| 2011/0292257 A1* | 12/2011 | Hatakeyama | H04N 5/208 348/E9.037 |
| 2012/0002422 A1 | 1/2012 | Lia et al. | |
| 2012/0062760 A1* | 3/2012 | Klapp | H04N 5/232 348/222.1 |
| 2012/0147165 A1 | 6/2012 | Yoshino et al. | |
| 2013/0070121 A1* | 3/2013 | Gu | H04N 5/2329 348/239 |
| 2013/0204084 A1* | 8/2013 | Hale | A61B 5/35 600/109 |
| 2013/0242129 A1* | 9/2013 | Harmeling | H04N 5/23229 348/222.1 |
| 2013/0338444 A1 | 12/2013 | Lia et al. | |
| 2014/0180001 A1* | 6/2014 | von Grunberg | A61B 1/00064 600/104 |
| 2014/0285676 A1 | 9/2014 | Barreto et al. | |
| 2014/0348441 A1* | 11/2014 | Tezaur | G06T 5/003 382/255 |
| 2014/0350338 A1* | 11/2014 | Tanaka | A61B 1/00193 600/111 |
| 2014/0354886 A1* | 12/2014 | Michaeli | G06T 5/003 348/607 |
| 2014/0355901 A1* | 12/2014 | Tezaur | G06T 5/003 382/255 |
| 2015/0042775 A1* | 2/2015 | Zhao | H04N 9/04515 348/71 |
| 2015/0172726 A1* | 6/2015 | Faramarzi | H04N 19/132 375/240.24 |
| 2015/0207962 A1* | 7/2015 | Sugimoto | G06T 3/4023 382/261 |
| 2015/0208051 A1* | 7/2015 | Sugimoto | G06T 5/003 348/223.1 |
| 2016/0005151 A1* | 1/2016 | Hatakeyama | G06T 5/001 348/241 |
| 2016/0051132 A1 | 2/2016 | Lia et al. | |
| 2016/0117806 A1* | 4/2016 | Hayashi | G06K 9/6215 382/218 |
| 2016/0150161 A1* | 5/2016 | Irie | H04N 5/243 348/229.1 |
| 2016/0171667 A1* | 6/2016 | Tezaur | G06T 5/003 382/275 |
| 2016/0180190 A1* | 6/2016 | Lifshin | H01J 37/28 382/201 |
| 2016/0192827 A1 | 7/2016 | Von Grünberg et al. | |
| 2017/0215716 A1 | 8/2017 | Lia et al. | |
| 2017/0261741 A1* | 9/2017 | Stoppe | H04N 5/2256 |

FOREIGN PATENT DOCUMENTS

| | | |
|---|---|---|
| JP | 63-131117 A | 6/1988 |
| JP | 7-359 A | 1/1995 |
| JP | 10-165365 A | 6/1998 |
| JP | 11-332820 A | 12/1999 |
| JP | 2010-226157 A | 10/2010 |
| JP | 2012-23498 A | 2/2012 |
| JP | 2012-125293 A | 7/2012 |
| JP | 2014-529389 A | 11/2014 |
| JP | 2015-139646 A | 8/2015 |
| JP | 2016505315 A | 2/2016 |

OTHER PUBLICATIONS

Partial Supplementary European Search Report dated Apr. 17, 2019 in Patent Application No. 17773536.2, 14 pages.

* cited by examiner

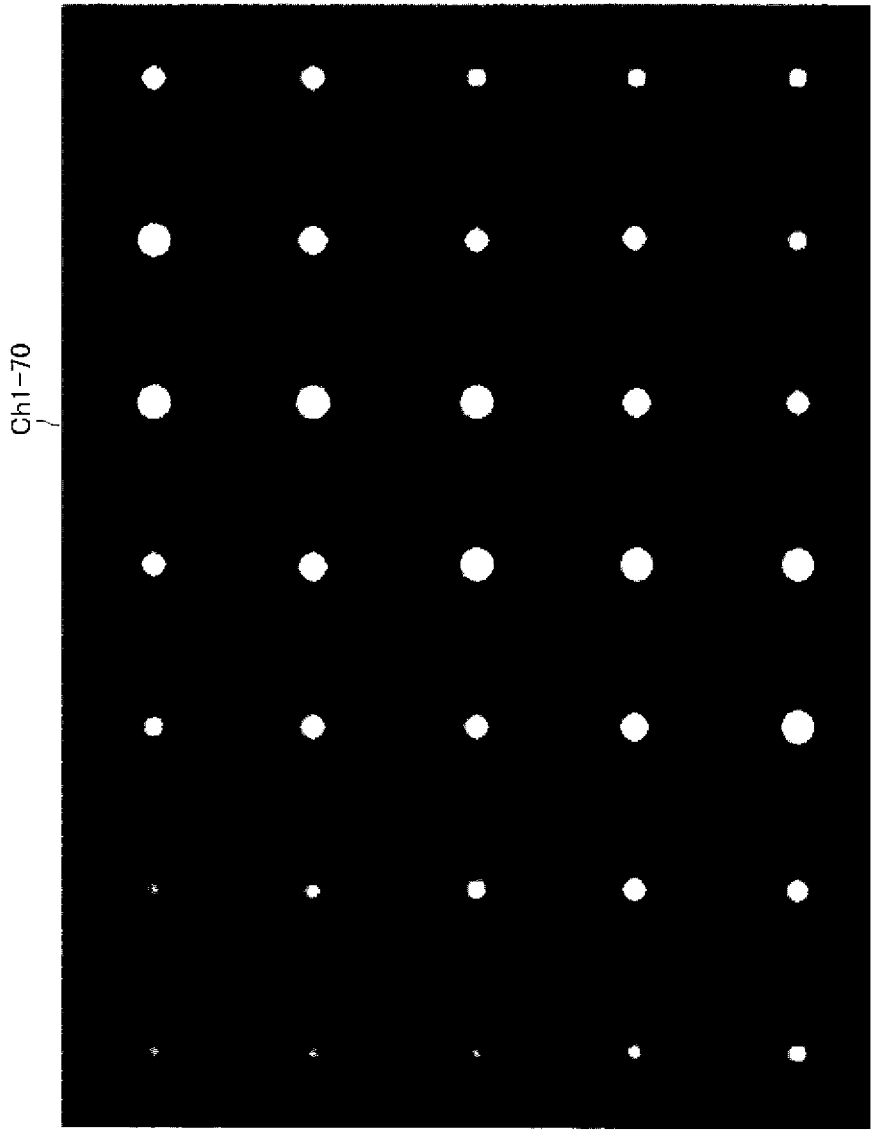

| | | |
|---|---|---|
| $L_1$ | $L_2$ | $L_3$ |
| $L_4$ | $L_5$ | $L_6$ |
| $L_7$ | $L_8$ | $L_9$ |

FIG. 34B

|  | 30-1 | 30-2 | 30-3 | 30-4 | 30-5 | 30-6 | 30-7 | 30-8 |
|---|---|---|---|---|---|---|---|---|
| 30 DEG | a | b | c | d | 0 | 0 | 0 | 0 |
| 70 DEG | 0 | 0 | e | f | g | h | 0 | 0 |
| 90 DEG | 0 | 0 | 0 | 0 | i | j | k | l |

CONTROL DEVICE, ENDOSCOPIC IMAGING DEVICE, CONTROL METHOD, PROGRAM, AND ENDOSCOPIC SYSTEM

TECHNICAL FIELD

The present disclosure relates to a control device, an endoscopic imaging device, a control method, a program, and an endoscopic system.

BACKGROUND ART

In recent years, various technologies concerning endoscopic devices have been disclosed. For example, a technology for estimating the center of rotation of an endoscopic device on the basis of a motion vector detected from an image captured by an image sensor and an angular velocity detected by a gyro sensor, and on the basis of the estimated center of rotation, performing image stabilization and obtaining a wide-viewing-angle image by stitching synthesis of images after image stabilization is disclosed (see Patent Literature 1, for example).

CITATION LIST

Patent Literature

Patent Literature 1: JP 2015-139646A

DISCLOSURE OF INVENTION

Technical Problem

However, in the case where an endoscopic device (hereinafter also referred to as a "variable-field-of-view endoscopic device") whose optical axis direction is variable is utilized, degradation in optical properties caused by a change in optical path may result in degradation in image quality of a captured image. Thus, it is desired that a technology that can reduce image quality degradation of an image captured by a variable-field-of-view endoscopic device is provided.

Solution to Problem

According to the present disclosure, there is provided a control device including: an image quality control unit configured to control image quality of an image for display on a basis of optical axis angle information with reference to a scope axis of an endoscope and an image signal acquired by an image sensor.

According to the present disclosure, there is provided a control method including: controlling image quality of an image for display on a basis of optical axis angle information with reference to a scope axis of an endoscope and an image signal acquired by an image sensor.

According to the present disclosure, there is provided a program for causing a computer to function as a control device including an image quality control unit configured to control image quality of an image for display on a basis of optical axis angle information with reference to a scope axis of an endoscope and an image signal acquired by an image sensor.

According to the present disclosure, there is provided an endoscopic system including: an endoscopic imaging device including a control device including an image quality control unit configured to control image quality of an image for display on a basis of optical axis angle information with reference to a scope axis of an endoscope and an image signal acquired by an image sensor, an angle control unit configured to control a light source angle with reference to the scope axis of the endoscope, and an imaging unit configured to image a subject in a body cavity during surgery to obtain an image signal. Information indicating the light source angle and the image signal are output to the control device.

Advantageous Effects of Invention

According to the present disclosure as described above, a technology that can reduce image quality degradation of an image captured by a variable-field-of-view endoscopic device is provided. Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 8C is a diagram showing an example of a chart captured image obtained in the case where a bent angle (rotation angle around a Y axis) of a rigid scope is 70 degrees.

FIG. 26 is a diagram for describing an example of a technique for generating luminance non-uniformity compensation data.

FIG. 32 is a diagram for describing an example of a technique for generating light distribution non-uniformity compensation data.

FIG. 34B is a diagram showing an example of light distribution non-uniformity compensation data.

MODE(S) FOR CARRYING OUT THE INVENTION

Figure 1:
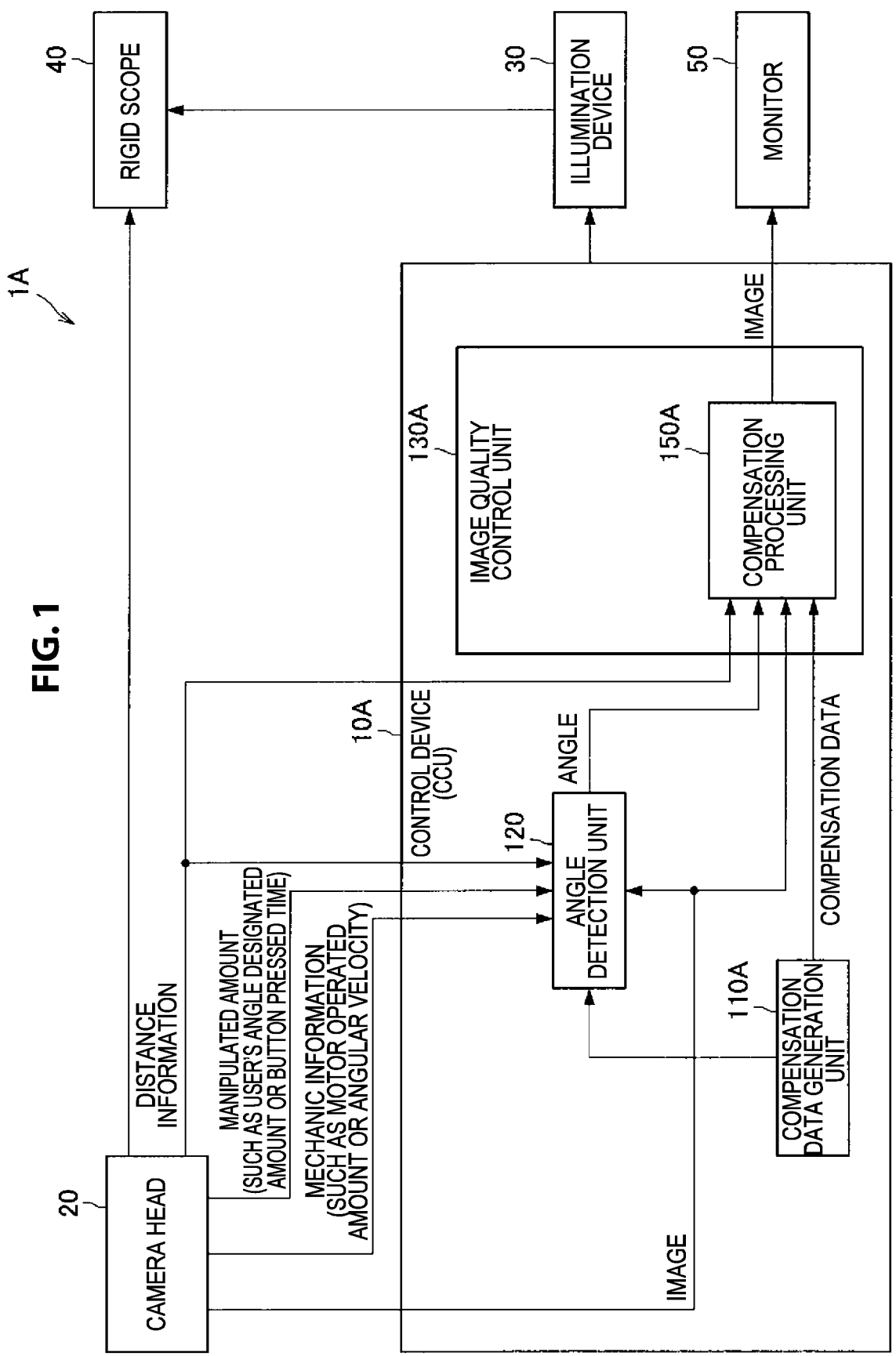
FIG. 1 is a diagram showing a configuration example of an endoscopic system according to a first embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that, in this description and the drawings, structural elements that have substantially the same function and structure are sometimes distinguished from each other using different numerals after the same reference sign. However, when there is no need in particular to distinguish structural elements that have substantially the same function and structure, the same reference sign alone is attached.

Note that description will be provided in the following order.

1. First Embodiment
1.1. System configuration example
1.2. Functional configuration example
1.3. Variants
2. Second Embodiment
2.1. System configuration example
2.2. Functional configuration example
2.3. Variants
3. Third Embodiment
3.1. System configuration example
3.2. Functional configuration example
3.3. Variants 4. Fourth Embodiment
4.1. System configuration example
4.2. Functional configuration example
4.3. Variants
5. Conclusion

1. First Embodiment

A first embodiment of the present disclosure will be described.

1.1. System Configuration Example

First, a configuration example of an endoscopic system (hereinafter also referred to as an "endoscopic device") according to a first embodiment of the present disclosure will be described. FIG. 1 is a diagram showing a configuration example of the endoscopic system according to the first embodiment of the present disclosure. As shown in FIG. 1, an endoscopic system 1A according to the first embodiment of the present disclosure includes a control device (Camera Control Unit (CCU)) 10A, a camera head 20, an illumination device 30, a rigid scope (hereinafter also referred to as a "scope") 40, and a monitor (display device) 50.

The control device 10A includes a compensation data generation unit 110A, an angle detection unit 120, and an image quality control unit 130A. The image quality control unit 130A has a compensation processing unit 150A. Note that, in an embodiment of the present disclosure, the case in which the functions of the control device 10A are achieved by a program read from a storage device (such as a magnetic storage unit device, a semiconductor storage device, an optical storage device, or a magneto-optical storage device, for example) being executed by an arithmetic unit is assumed, whilst the functions of the control device 10A may be achieved by dedicated hardware (a dedicated electronic circuit).

The monitor 50 has the function of displaying a screen in accordance with control by the control device 10A. For example, the monitor 50 may be a liquid crystal display, an organic electro-luminescence (EL) display, or a projector. However, the monitor 50 may be a display device of another form as long as the monitor 50 has the function of displaying a screen in accordance with control by the control device 10A.

Figure 2:
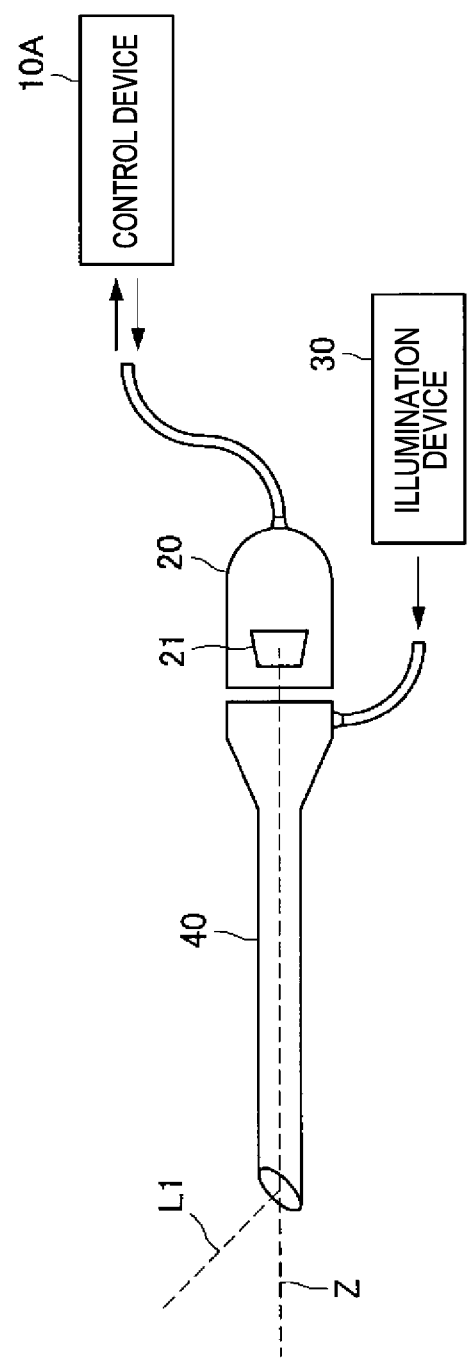
FIG. 2 is a diagram showing a configuration example of a rigid scope and a camera head.
Figure 3:
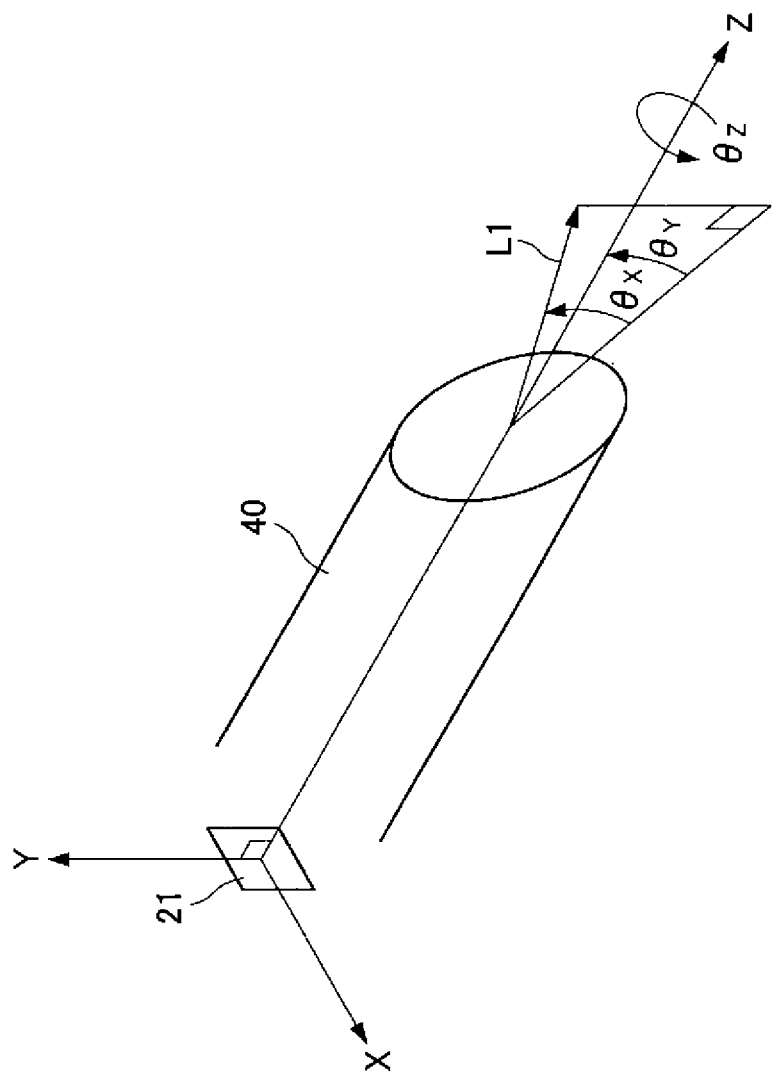
FIG. 3 is a diagram for describing an expression example of an optical axis angle.
Figure 4:
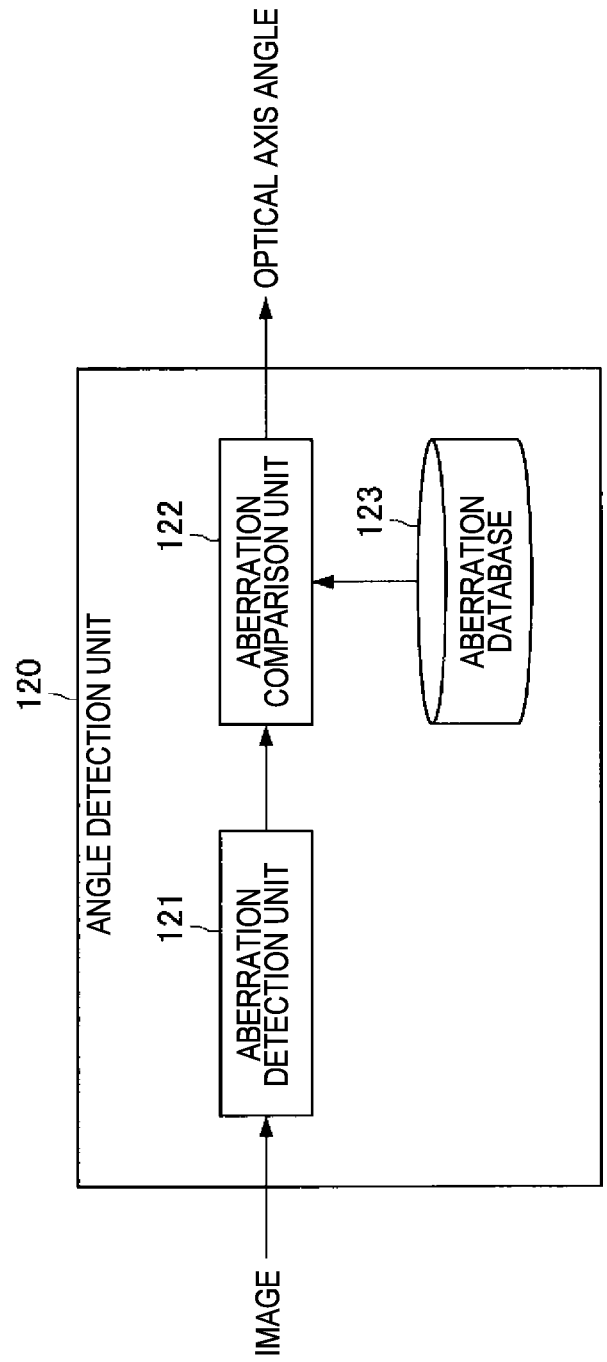
FIG. 4 is a diagram showing a detailed configuration example of an angle detection unit in the case of adopting a fourth angle detection technique.

Basic functions of the endoscopic system 1A will be described with reference to FIG. 2 to FIG. 4. FIG. 2 is a diagram showing a configuration example of the rigid scope 40 and the camera head 20. As shown in FIG. 2, light emitted from the illumination device 30 passes through the inside of the rigid scope 40, and a subject present outside the rigid scope 40 is irradiated. Here, in an embodiment of the present disclosure, the case in which an angle (hereinafter also simply referred to as a "light source angle") with reference to a predetermined direction of light emitted from a light source of the illumination device 30 is variable is assumed, whilst the light source angle may be fixed (except a fourth embodiment of the present disclosure).

An image sensor (imaging unit) 21 is incorporated in the camera head 20, and when light having been reflected on the subject and passed through the inside of the rigid scope 40 along an optical axis L1 is incident, the image sensor 21 converts the incident light into an electric signal. Imaging of the subject is achieved by the function of such an image sensor 21. Here, in an embodiment of the present disclosure, the case in which a bent angle and rotation angle of the optical axis L1 with reference to a scope axis Z (hereinafter both of the bent angle and rotation angle will also be referred to as an "optical axis angle") may be changed by the function of an angle control unit in accordance with a user manipulation is assumed. In addition, in an embodiment of the present disclosure, the case in which a user manipulation is input to the camera head 20 is assumed, whilst the position at which the user manipulation is input is not particularly limited.

In addition, in an embodiment of the present disclosure, the case in which the image sensor 21 has a 3-dimensional (D) imaging function, and a distance information calculation unit enables information about the distance to a subject (a depth map of a so-called imaging scene) to be acquired by this 3D imaging function is assumed. However, a technique for acquiring information about the distance to a subject is not particularly limited. For example, a predetermined device different from the image sensor 21 may have the function of acquiring information about the distance to a subject. Information indicating the optical axis angle (hereinafter also referred to as an "optical axis angle") and an image captured by the image sensor 21 are output to the control device 10A. At this time, in the case where an R signal, a G signal, and a B signal are obtained by the image sensor 21, the R signal, G signal, and B signal are output to the control device 10A. In addition, in the case where a chart which will be described later is imaged by the image sensor 21, a chart image signal is output to the control device 10A.

Here, an expression example of an optical axis angle will be described. FIG. 3 is a diagram for describing an expression example of the optical axis angle. As shown in FIG. 3, after passing through the inside of the rigid scope 40, light reflected on the subject is incident on the image sensor 21 perpendicularly. In addition, as shown in FIG. 3, assuming that two axes perpendicular to the scope axis Z are an X axis and a Y axis, respectively, the optical axis L1 is expressed by a rotation angle $\theta X$ around the X axis, a rotation angle $\theta Y$ around the Y axis, and a rotation angle $\theta Z$ around the Z axis.

Detection of such an optical axis angle is executed by the angle detection unit 120. Here, various techniques may be applied to a technique for detecting the optical axis angle. As a first angle detection technique, the angle detection unit 120 is capable of detecting the optical axis angle on the basis of a manipulated amount transmitted from the camera head 20 (optical axis angle information may be information controlled by the imaging device). More specifically, as shown in FIG. 1, in the case where the optical axis angle can be directly designated by a user manipulation, the angle detection unit 120 may detect the optical axis angle on the basis of the designated optical axis angle (an angle designated amount).

Alternatively, in the case where a button that causes the optical axis angle to change in association with the length of a pressed time is provided, the angle detection unit 120 may detect the optical axis angle on the basis of the length of the time during which the button is pressed. Alternatively, in the case where a manipulation unit that causes the optical axis angle to change in association with the length of a manipulation time is provided for the camera head 20, the angle detection unit 120 may detect the optical axis angle on the basis of the length of a manipulation time detected by a predetermined sensor (such as an angle detection sensor or a pressure sensor, for example) provided for the manipulation unit.

In addition, as a second angle detection technique, the angle detection unit 120 is capable of detecting the optical axis angle on the basis of mechanical information (hereinafter also referred to as "mechanic information") transmitted from the camera head 20 (optical axis angle information may be information detected by an angle detection device). More specifically, as shown in FIG. 1, the angle detection unit 120 may detect the optical axis angle on the basis of the operated amount of a rotation driving motor of the optical axis. Alternatively, the angle detection unit 120 may detect the optical axis angle by calculating a position attitude of the rigid scope 40 on the basis of sensor information detected by a predetermined sensor (such as a gyro sensor, an acceleration sensor, an azimuth sensor, or an optical type or a magnetic type position acquisition sensor, for example) provided for the rigid scope 40.

In addition, as a third angle detection technique, the angle detection unit 120 is capable of detecting the optical axis angle on the basis of an image transmitted from the camera head 20. More specifically, in the case where a target object to be imaged stays still, it is generally known that, by capturing two images (an image from a first viewpoint and an image from a second viewpoint) from different viewpoints and obtaining an external camera parameter from corresponding points between the two images, relative position attitudes of the first viewpoint and the second viewpoint may be calculated.

Therefore, the angle detection unit 120 is capable of sequentially continuing detecting relative position attitudes in the time direction in the case where a target object to be imaged stays still, and by integrating the position attitudes, obtaining the amount of change in position attitude of the rigid scope 40 with reference to a certain starting time point. Such a technology of concurrently performing self-position estimation and environmental map generation is called Simultaneous Localization and Mapping (SLAM), and the angle detection unit 120 is capable of obtaining the optical axis angle by using the SLAM technology.

In addition, a fourth angle detection technique includes a technique for utilizing a change in aberration caused by a change in optical axis angle. That is, the angle detection unit 120 is capable of detecting the optical axis angle on the basis of a change in aberration. Here, aberrations changed by a change in optical axis angle include distortion, field curvature aberration, astigmatism, and the like. FIG. 4 is a diagram showing a detailed configuration example of the angle detection unit 120 in the case of adopting the fourth angle detection technique. As shown in FIG. 4, the angle detection unit 120 in the case of adopting the fourth angle detection technique has an aberration detection unit 121, an aberration comparison unit 122, and an aberration database 123.

The aberration detection unit 121 acquires an image signal (hereinafter also referred to as an "image") captured by the image sensor 21, and analyzes the acquired image to calculate aberration information. In the aberration database 123, aberration information measured previously for each of a plurality of optical axis angles are recorded together with corresponding optical axis angles. The aberration comparison unit 122 acquires an optical axis angle corresponding to aberration information having the highest degree of agreement with aberration information calculated by the aberration detection unit 121 from the aberration database 123. For example, the aberration detection unit 121 acquires chromatic aberration information in the vicinity of a luminescent spot of an image through an image analysis, and the aberration comparison unit 122 acquires an optical axis angle corresponding to chromatic aberration information having the highest degree of agreement with the chromatic aberration information acquired by the aberration detection unit 121 from the aberration database 123.

1.2. Functional Configuration Example

The basic functions of the endoscopic system 1A have been described above with reference to FIG. 2 to FIG. 4. Here, as described above, in an embodiment of the present disclosure, the case in which the optical axis angle is variable is assumed. In such a case, the image quality of an image captured by the image sensor 21 may be degraded because of degradation in optical properties caused by a change in optical path. In an embodiment of the present disclosure, a technology that can reduce image quality degradation of an image captured by a variable-field-of-view endoscopic device will be mainly proposed.

More specifically, in the case where the optical axis angle is variable, an optical path in an angle adjusting portion changes subtly per bent angle (the rotation angle $\theta X$ around the X axis, the rotation angle $\theta Y$ around the Y axis) and rotation angle (the rotation angle $\theta Z$ around the Z axis), and degradation in optical properties may occur in that the refractive index varies per wavelength of light, a difference occurs in reflectance, or optical axis displacement occurs, for example. Then, influences of errors due to degradation in these optical properties accumulate, and the image quality may be degraded depending on the bent angle and rotation angle. The first embodiment of the present disclosure mainly proposes a technology of reducing such image quality degradation (in particular, blur non-uniformity) that occurs depending on the bent angle and rotation angle.

Figure 5:
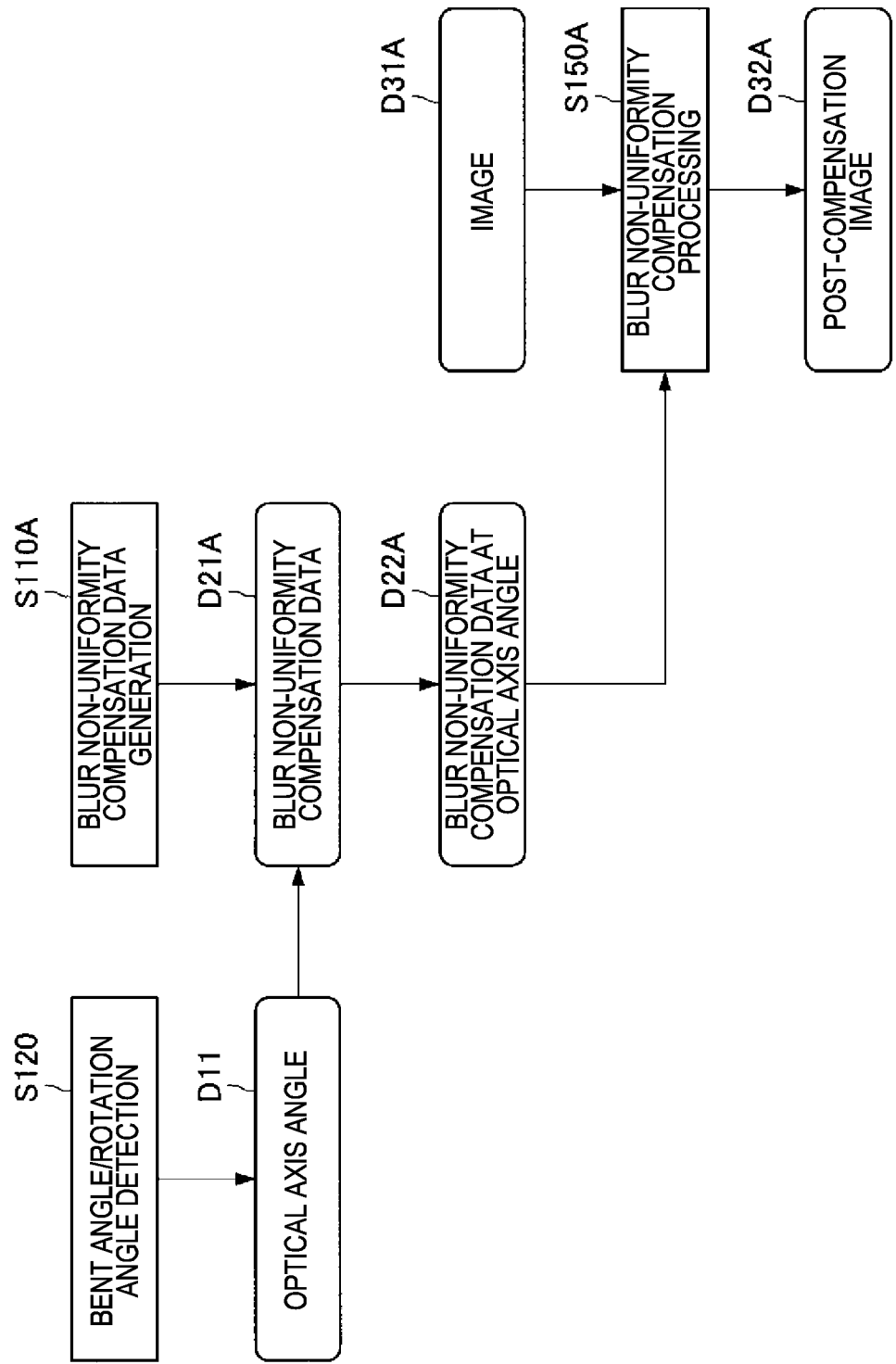
FIG. 5 is a flowchart showing an operation example of a control device according to the first embodiment of the present disclosure.

FIG. 5 is a flowchart showing an operation example of the control device 10A according to the first embodiment of the present disclosure. First, as shown in FIG. 5, the compensation data generation unit 110A (FIG. 1) generates blur non-uniformity compensation data D21A in blur non-uniformity compensation data generation S110A. Here, a specific example of the blur non-uniformity compensation data generation S110A by the compensation data generation unit 110A will be described.

Figure 6:
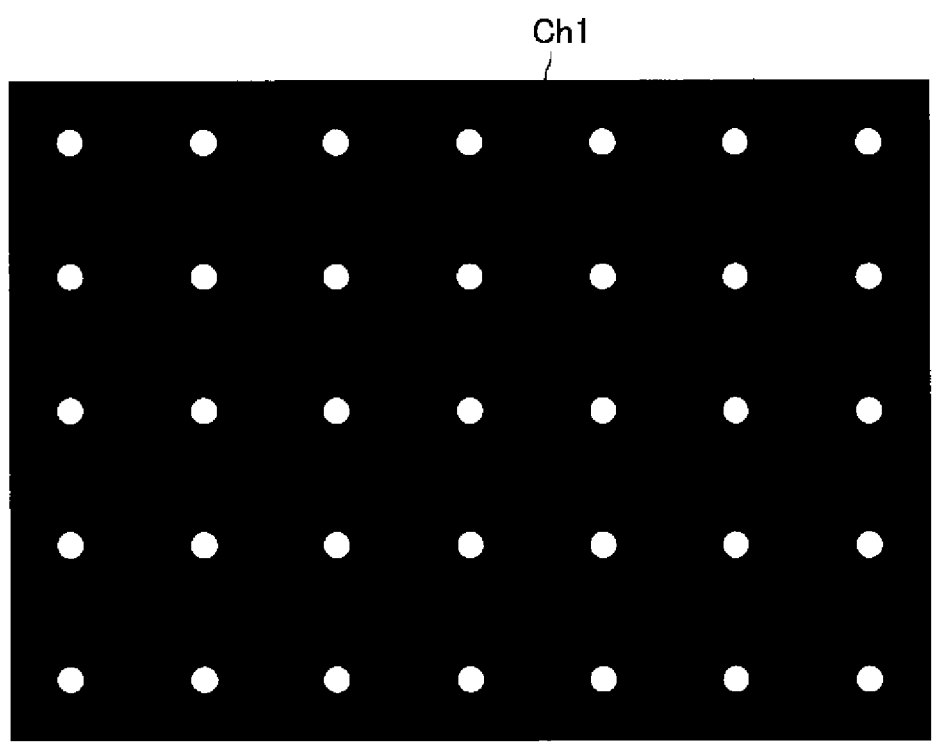
FIG. 6 is a diagram showing an example of a chart that can be utilized for generation of blur non-uniformity compensation data.

FIG. 6 is a diagram showing an example of a chart that can be utilized for generation of blur non-uniformity compensation data. As shown in FIG. 6, a plurality of dots are arranged in a chart Ch1 that can be utilized for generation of blur non-uniformity compensation data. Here, it is desirable that the dot color is white and the background color is black, whilst the color of each of dots and background is not particularly limited. In addition, the manner in which a plurality of dots are arranged is also not particularly limited. In addition, in the example shown in FIG. 6, the shape of each of the plurality of dots is circular, whilst the shape of each of the plurality of dots is not particularly limited.

Figure 7:
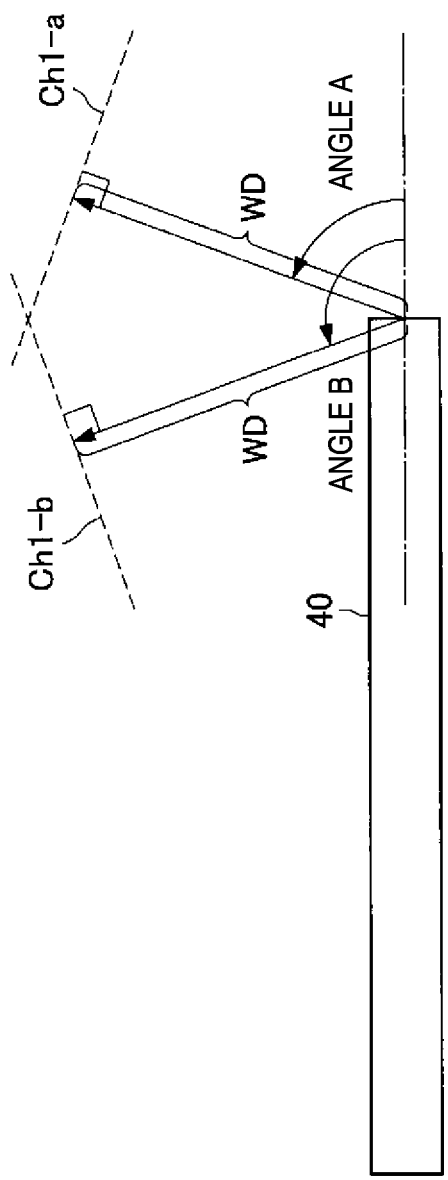
FIG. 7 is a diagram for describing an example of imaging a chart.

When such a chart Ch1 is previously imaged by the image sensor 21, an image (hereinafter also referred to as a "chart captured image") is obtained. An example of imaging the chart Ch1 will be described. FIG. 7 is a diagram for describing an example of imaging the chart Ch1. With reference to FIG. 7, in the case where the bent angle (the rotation angle $\theta Y$ around the Y axis) of the rigid scope 40 is an angle A, a chart Ch1-*a* placed in a direction perpendicular to the optical axis and at a position away from the rigid scope 40 by a Working Distance (WD) frequently used for imaging is imaged.

Similarly, in the case where the bent angle (the rotation angle $\theta Y$ around the Y axis) of the rigid scope 40 is an angle B, a chart Ch1-*b* placed in a direction perpendicular to the optical axis and at a position away from the rigid scope 40 by the distance WD frequently used for imaging is imaged. FIG. 7 shows an example in which only two images of the chart Ch1 are captured while changing the bent angle (the rotation angle θY around the Y axis), whilst with a similar technique, a plurality of images of the chart Ch1 are captured while changing the bent angle (the rotation angle θY around the Y axis).

Figure 8A:
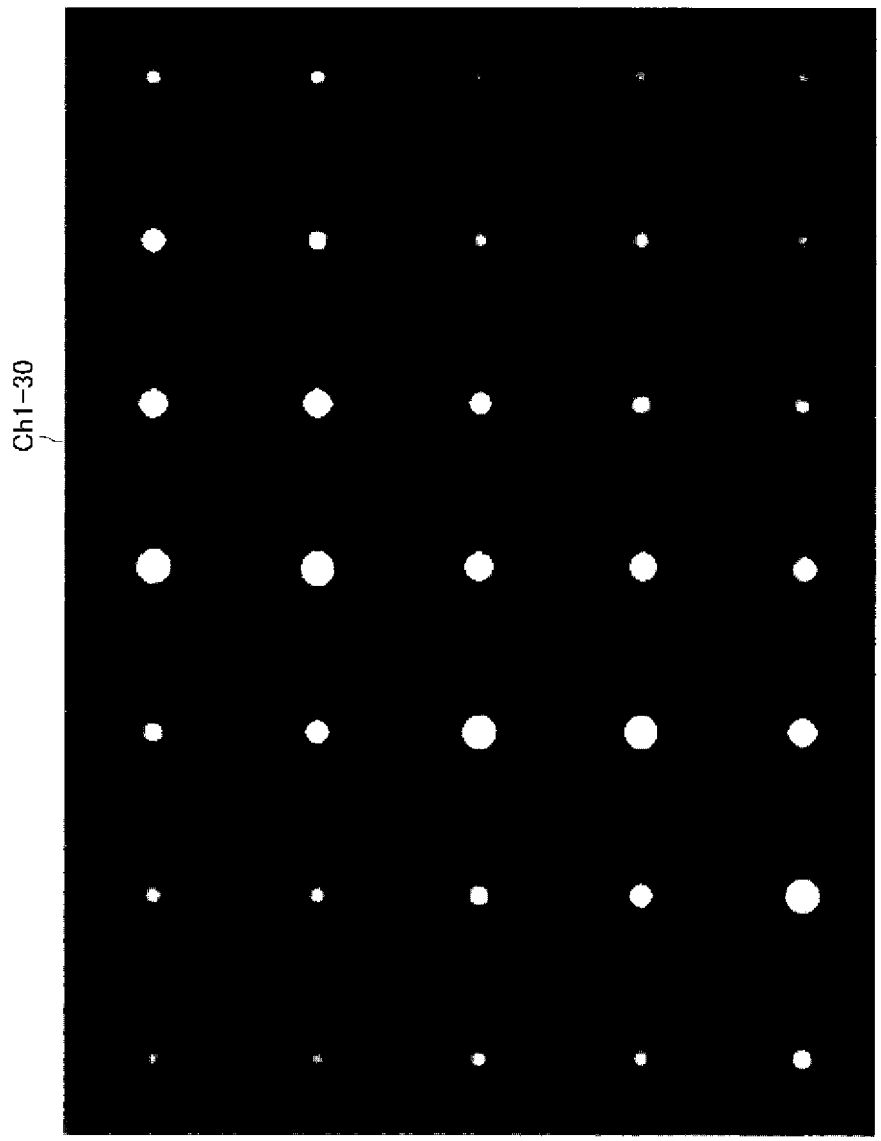
FIG. 8A is a diagram showing an example of a chart captured image obtained in the case where a bent angle (rotation angle around a Y axis) of a rigid scope is 30 degrees.
Figure 8B:
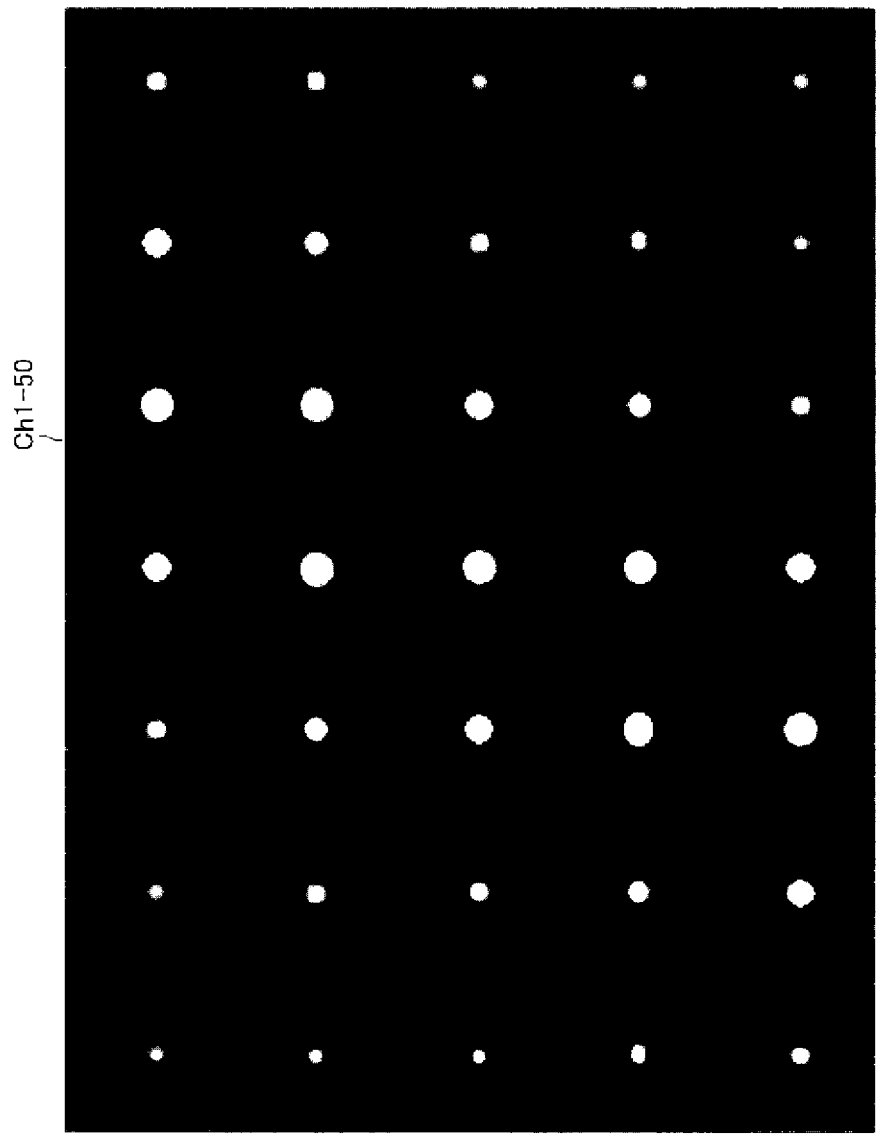
FIG. 8B is a diagram showing an example of a chart captured image obtained in the case where a bent angle (rotation angle around a Y axis) of a rigid scope is 50 degrees.

FIG. 8A is a diagram showing an example of a chart captured image Ch1-30 obtained in the case where the bent angle (the rotation angle θY around the Y axis) of the rigid scope 40 is 30 degrees. FIG. 8B is a diagram showing an example of a chart captured image Ch1-50 obtained in the case where the bent angle (the rotation angle θY around the Y axis) of the rigid scope 40 is 50 degrees. FIG. 8C is a diagram showing an example of a chart captured image Ch1-70 obtained in the case where the bent angle (the rotation angle θY around the Y axis) of the rigid scope 40 is 70 degrees.

Figure 8D:
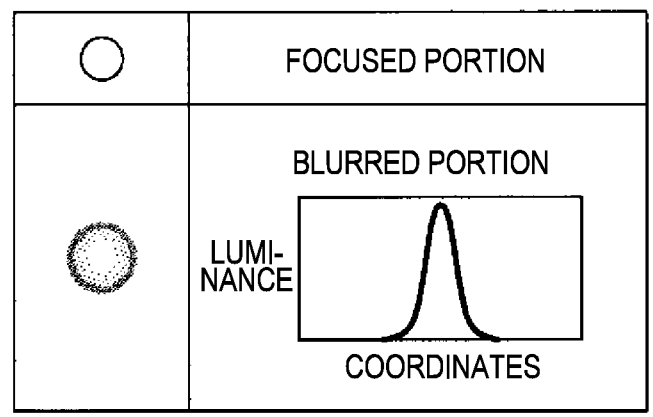
FIG. 8D is a diagram showing an example of a focused portion and a blurred portion.

FIG. 8D is a diagram showing an example of a focused portion and a blurred portion. As described in FIG. 8D, in the focused portion, the contour of dots appears clearly. On the other hand, in the blurred portion, the luminance increases gradually from the outer side to the inner side of dots. With reference to the chart captured image Ch1-30, the chart captured image Ch1-50, and the chart captured image Ch1-70 considering such characteristics, it is understood that blur non-uniformity changes in accordance with changes in bent angle (the rotation angle θY around the Y axis).

Note that the examples of capturing a plurality of images of the chart Ch1 while changing the bent angle (the rotation angle θY around the Y axis) have been representatively described in FIG. 7 and FIG. 8A to FIG. 8C, whilst an angle to be changed is not only the bent angle (the rotation angle θY around the Y axis). That is, with a technique similar to the technique described with reference to FIG. 7 and FIG. 8A to FIG. 8C, a plurality of images of the chart Ch1 are captured while changing the bent angle (the rotation angle θX around the X axis), and a plurality of images of the chart Ch1 are captured while changing the rotation angle (the rotation angle θZ around the Z axis).

Figure 9A:
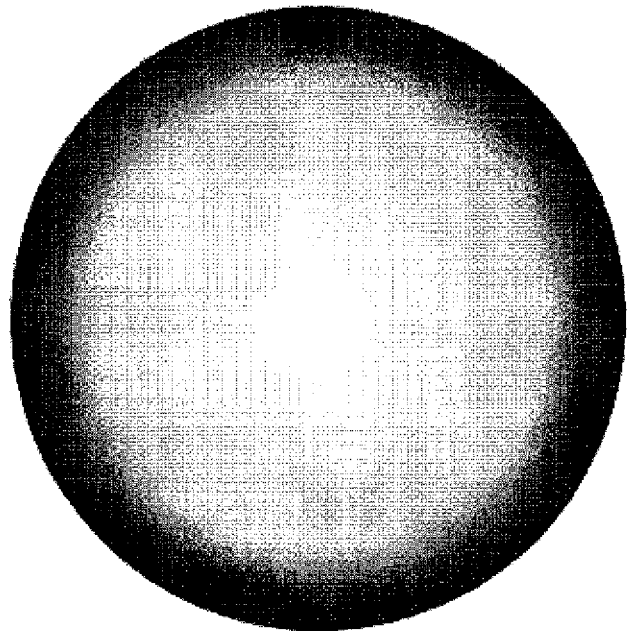
FIG. 9A is a diagram showing an example of dots appearing in a chart captured image.
Figure 9B:
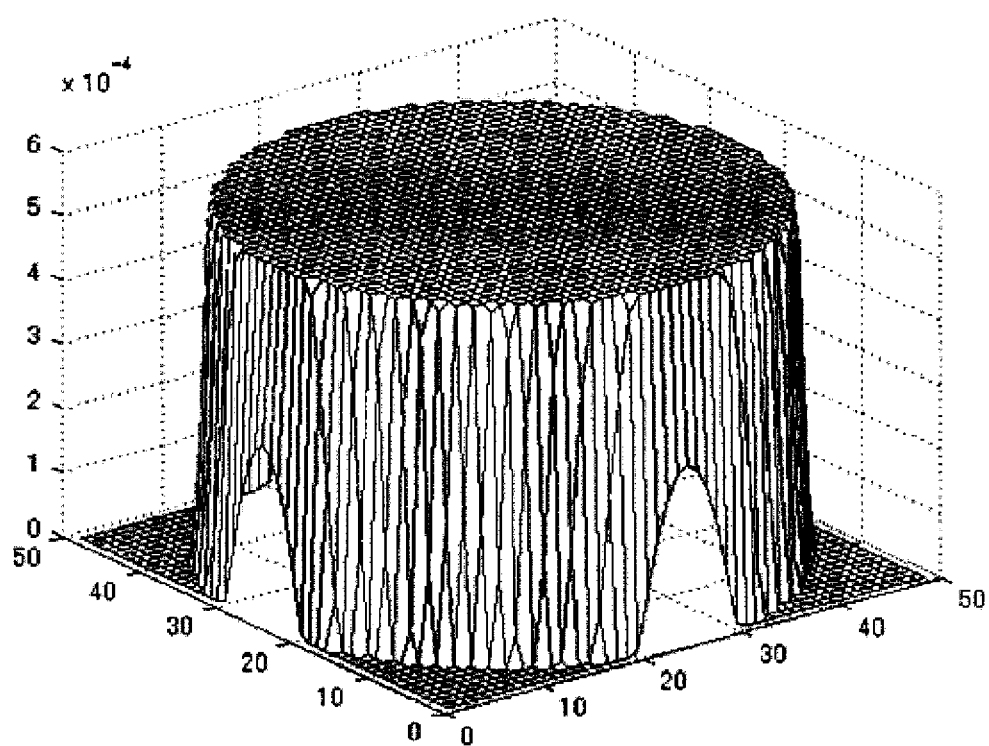
FIG. 9B is a diagram showing an example of a Pill Box function.
Figure 9C:
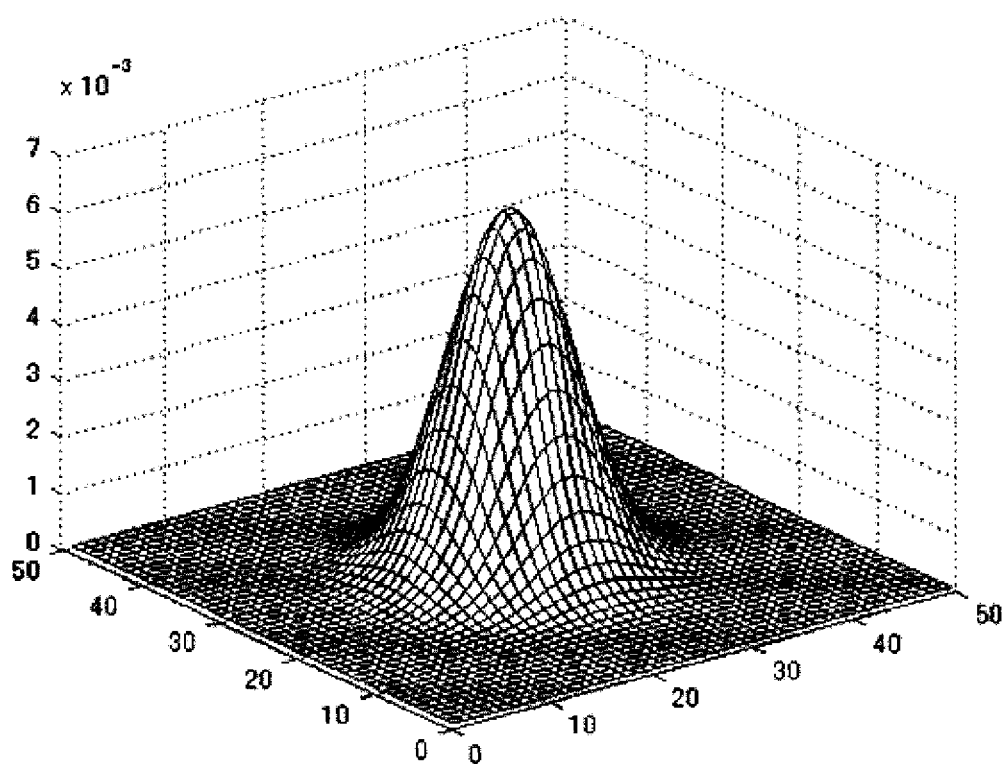
FIG. 9C is a diagram showing an example of a Gaussian function.

The compensation data generation unit 110A estimates a Point Spread Function (PSF) that changes depending on a spatial position on the basis of a chart captured image. The technique for estimating the point spread function is not limited. Here, an example of the technique for estimating the point spread function will be described. FIG. 9A is a diagram showing an example of dots appearing in a chart captured image. FIG. 9B is a diagram showing an example of a Pill Box function. FIG. 9C is a diagram showing an example of a Gaussian function. For example, the compensation data generation unit 110A may estimate the point spread function by approximating the dots shown in FIG. 9A to the Pill Box function (FIG. 9B) or the Gaussian function (FIG. 9C).

Subsequently, the compensation data generation unit 110A generates the blur non-uniformity compensation data D21A on the basis of the estimated point spread function. Here, assuming that the estimated point spread function is h, and true image data without blur is f, image data g acquired by the compensation data generation unit 110A from the image sensor 21 is expressed by a convolution of f and h (Formula 2) as indicated in (Formula 1) below.

[Math. 1]

$$g = f \otimes h \quad \text{(Formula 1)}$$

[Math. 2]

$$\otimes \quad \text{(Formula 2)}$$

Assuming that a matrix expressing h by a fixed tap number is A, the image data g acquired by the compensation data generation unit 110A from the image sensor 21 is expressed as indicated in (Formula 3) below.

[Math. 3]

$$g = A \cdot f \quad \text{(Formula 3)}$$

The compensation data generation unit 110A is capable of obtaining an estimated value of true image data (Formula 5) by multiplying the both sides of (Formula 3) by the inverse matrix of A, as indicated in (Formula 4) below.

[Math. 4]

$$A^{-1} \cdot A \hat{f} = A^{-1} \cdot g \quad \text{(Formula 4)}$$

[Math. 5]

$$\hat{f} = A^{-1} \cdot g \quad \text{(Formula 5)}$$

Figure 10:
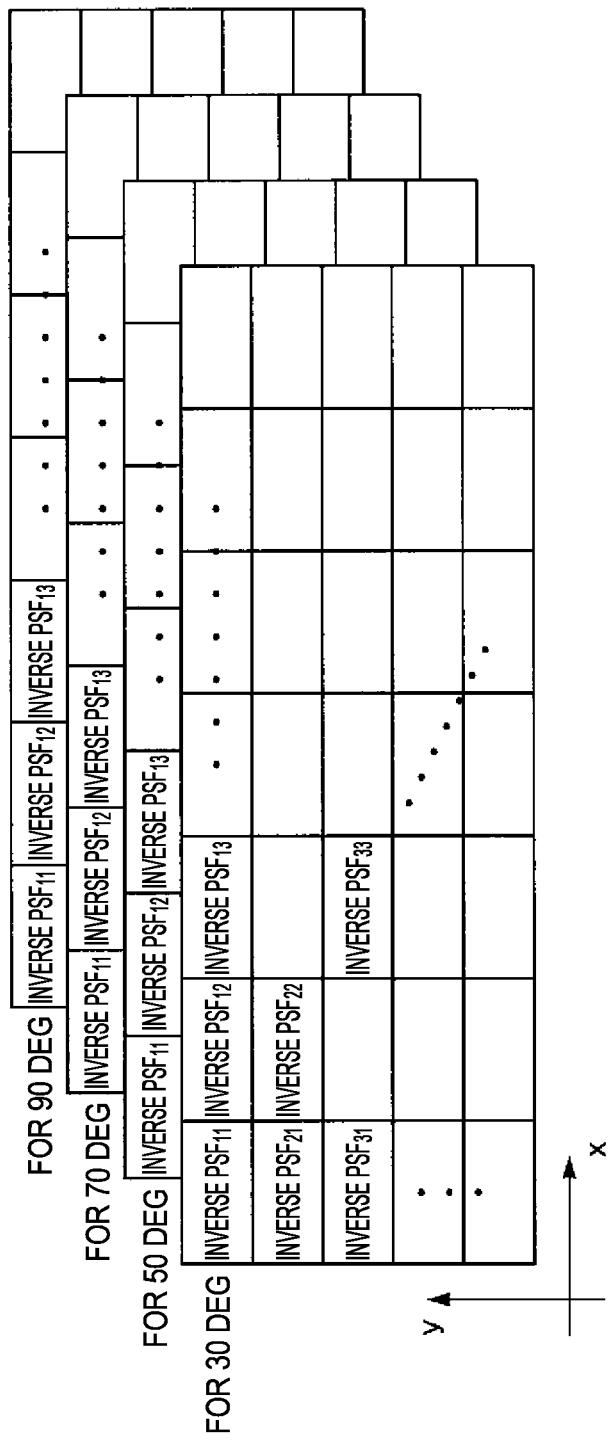
FIG. 10 is a diagram showing an example of blur non-uniformity compensation data.

In this manner, the compensation data generation unit 110A is capable of obtaining the inverse matrix of A as blur non-uniformity compensation data. FIG. 10 is a diagram showing an example of blur non-uniformity compensation data. With reference to FIG. 10, in each of the cases where the bent angle (the rotation angle θY around the Y axis) is 30 degrees, 50 degrees, 70 degrees, and 90 degrees, an estimated value of true image data is shown per pixel.

Note that the example in which the bent angle (the rotation angle θX around the X axis) and the rotation angle (the rotation angle θZ around the Z axis) are fixed and the bent angle (the rotation angle θY around the Y axis) is changed is shown here. However, the bent angle (the rotation angle θX around the X axis) and the rotation angle (the rotation angle θZ around the Z axis) may also be changed similarly to the bent angle (the rotation angle θY around the Y axis), as described above.

Description will be continued returning to FIG. 5. The angle detection unit 120 detects an optical axis angle (bent angle and rotation angle) D11 in bent angle/rotation angle detection 5120. Subsequently, the image quality control unit 130A controls the image quality of an image D31A captured by the image sensor 21 on the basis of the optical axis angle D11 (the image quality control unit 130A controls the image quality of an image for display on the basis of the image D31A captured by the image sensor 21 and optical axis angle information). With such a configuration, it is possible to reduce image quality degradation that occurs depending on the bent angle and the rotation angle.

For example, the image quality control unit 130A controls the image quality of the image D31A by subjecting the image D31A captured by the image sensor 21 to predetermined image processing at least based on the optical axis angle. In particular, in the first embodiment of the present disclosure, the image quality control unit 130A performs the predetermined image processing by compensating blur non-uniformity of the image D31A on the basis of the optical axis angle. With such a configuration, it is possible to reduce blur non-uniformity that occurs depending on the optical axis angle.

The image quality control unit 130A acquires, with the compensation processing unit 150A, data (blur non-uniformity compensation data D22A at the optical axis angle) corresponding to the optical axis angle on the basis of the blur non-uniformity compensation data D21A previously generated, and compensates blur non-uniformity of the image D31A on the basis of the acquired data and the image D31A captured by the image sensor 21 in blur non-uniformity compensation processing S150A. Accordingly, a post-compensation image D32A is obtained.

More specifically, the image quality control unit 130A compensates blur non-uniformity by multiplying, with the compensation processing unit 150A, the image D31A captured by the image sensor 21 and blur non-uniformity compensation data as shown in FIG. 10 (that is, by deconvoluting inverse PSF data to the image D31A). Note that, since the blur non-uniformity compensation data exists discretely in space, data not directly existing as blur non-uniformity compensation data is obtained by interpolation or extrapolation from directly existing blur non-uniformity compensation data.

1.3. Variants

Various variants may be applied to the first embodiment of the present disclosure. For example, a technique for obtaining a post-compensation image D32-1 by Deconvolution has been described above. However, the technique for obtaining the post-compensation image D32-1 by Deconvolution is not limited to the above-described example. That is, in the first embodiment of the present disclosure, every well-known Deconvolution may be applied in order to obtain the post-compensation image D32-1.

Figure 11:
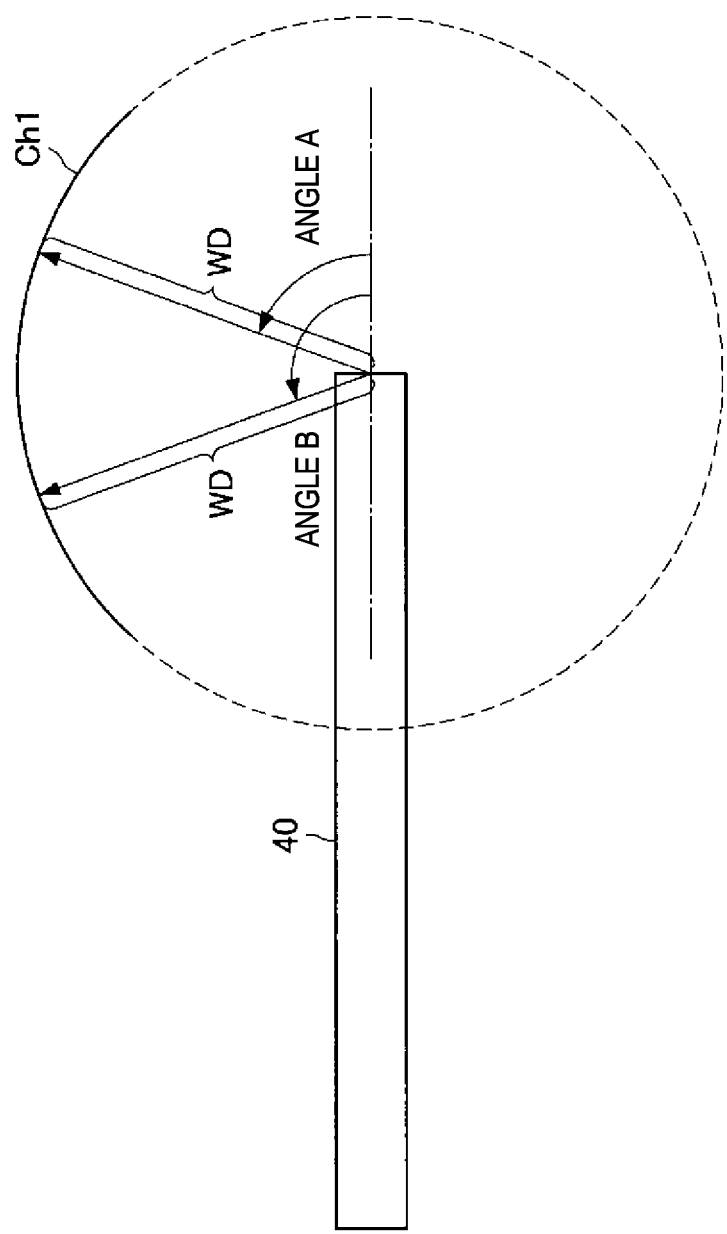
FIG. 11 is a diagram for describing another example of imaging a chart.

In addition, the example in which a plurality of images of a chart are captured while moving the chart of planar shape has been described above. However, the shape of the chart is not limited to the planar shape. For example, the shape of the chart may be a curved surface shape. FIG. 11 is a diagram for describing another example of imaging the chart Ch1. As shown in FIG. 11, the chart Ch1 may have a curved surface shape. At this time, as shown in FIG. 11, the chart Ch1 having a curved surface shape may be placed along a position away from the rigid scope 40 by the distance WD frequently used for imaging.

In addition, the example in which the chart placed at a position away from the rigid scope 40 by the distance WD frequently used for imaging is imaged has been described above. However, the position at which the chart is placed is not limited to the position away from the rigid scope 40 by the distance WD frequently used for imaging. For example, the compensation data generation unit 110A may associate the distance from the rigid scope 40 when imaging the chart with the optical axis angle when imaging the chart and blur non-uniformity compensation data.

At this time, as described above, as long as information about the distance to a subject (a depth map of a so-called imaging scene) can be acquired, the image quality control unit 130A is capable of acquiring, with the compensation processing unit 150A, distance information indicating the distance to the subject, and acquiring data corresponding to the distance information and optical axis angle on the basis of blur non-uniformity compensation data. If the distance information is also considered in this manner, it is expected that the accuracy of blur non-uniformity compensation is improved.

Figure 12A:
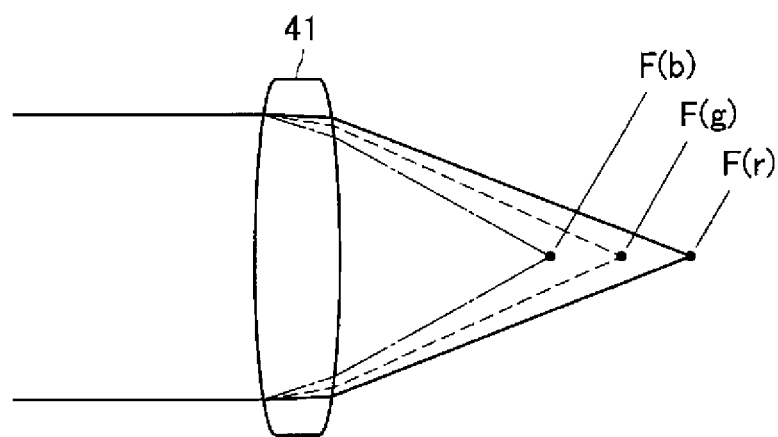
FIG. 12A is a diagram showing an example of an optical path per wavelength.

In addition, the case in which color imaging has been performed is not particularly considered above, whilst the case in which color imaging has been performed may be considered. FIG. 12A is a diagram showing an example of an optical path per wavelength. With reference to FIG. 12A, an optical path of blue light is indicated as F(b), an optical path of green light is indicated as F(g), and an optical path of red light is indicated as F(r). In this manner, since the focal length of light passed through the lens 41 is changed by the wavelength of light, chromatic aberration blur due to on-axis chromatic aberration may occur during color imaging.

Figure 12B:
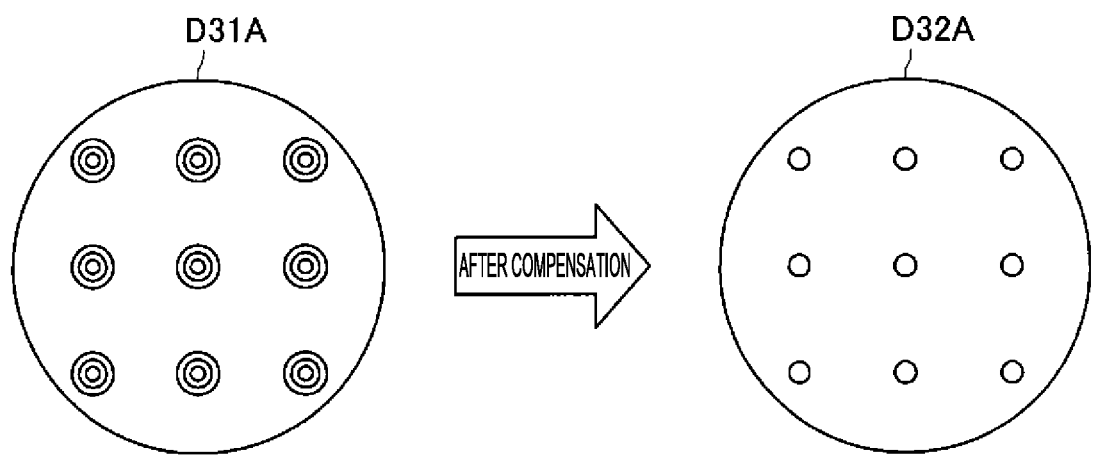
FIG. 12B is a diagram showing an example of images before and after blur non-uniformity compensation is performed for all RGB values.

Therefore, in the case where an image has RGB values, the image quality control unit 130A may perform, with the compensation processing unit 150A, image processing (in the first embodiment of the present disclosure, blur non-uniformity compensation) for all the RGB values. Then, it is possible to reduce chromatic aberration blur due to on-axis chromatic aberration. FIG. 12B is a diagram showing an example of images before and after blur non-uniformity compensation is performed for all the RGB values. With reference to FIG. 12B, it is understood that chromatic aberration blur has occurred in the image D31A captured by the image sensor 21, while chromatic aberration blur has been reduced in the post-compensation image D32A.

The first embodiment of the present disclosure has been described above.

2. Second Embodiment

Subsequently, a second embodiment of the present disclosure will be described.

2.1. System Configuration Example

Figure 13:
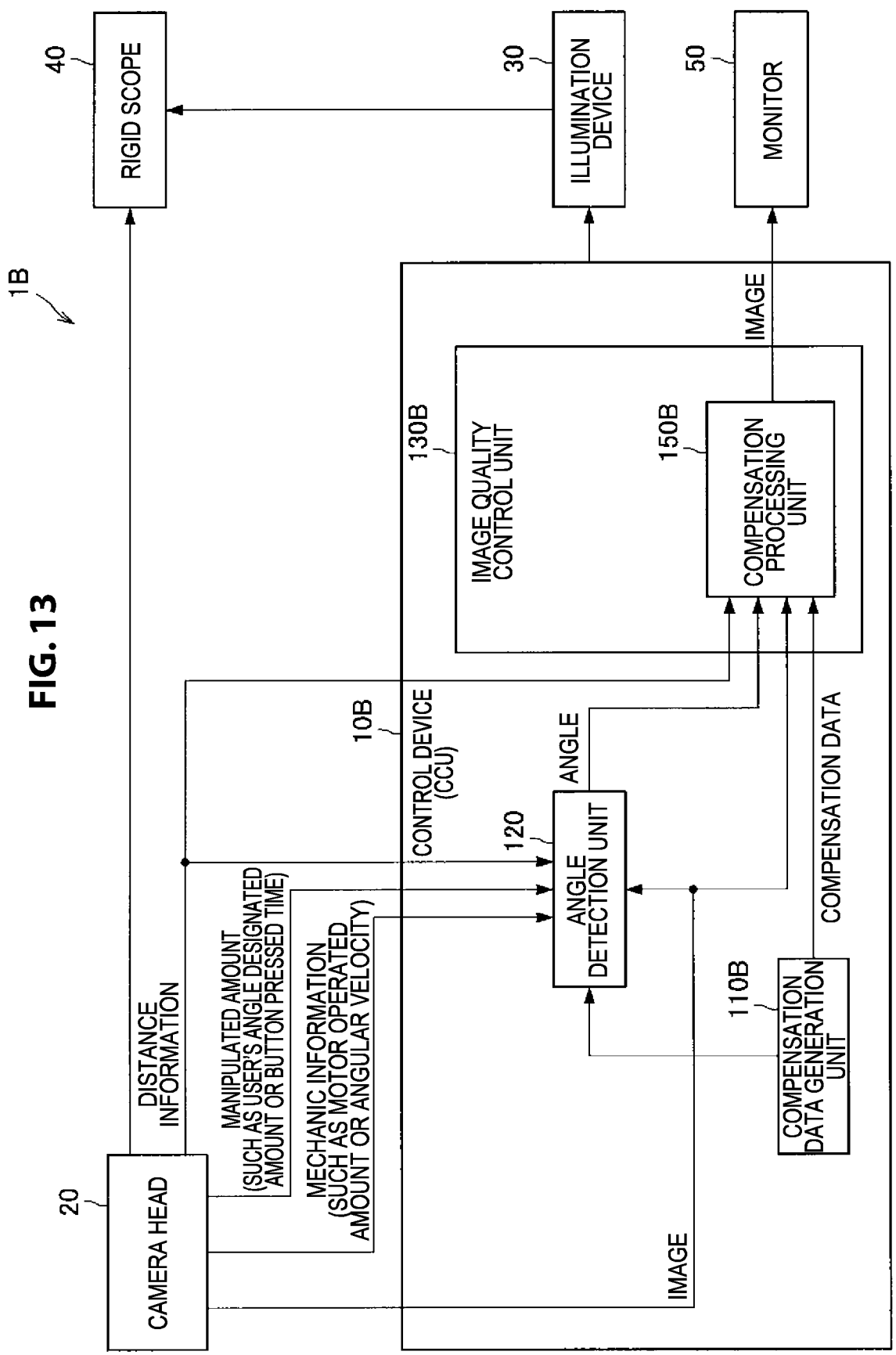
FIG. 13 is a diagram showing a configuration example of an endoscopic system according to a second embodiment of the present disclosure.

First, a configuration example of an endoscopic system according to the second embodiment of the present disclosure will be described. FIG. 13 is a diagram showing a configuration example of an endoscopic system according to the second embodiment of the present disclosure. The first embodiment of the present disclosure and the second embodiment of the present disclosure are different in that the endoscopic system 1A includes the control device 10A with reference to FIG. 1, while an endoscopic system 1B includes a control device 10B with reference to FIG. 13. The other components are substantially identical between the first embodiment of the present disclosure and the second embodiment of the present disclosure. Thus, in the second embodiment of the present disclosure, the control device 10B will be mainly described.

In addition, the first embodiment of the present disclosure and the second embodiment of the present disclosure are different in that the control device 10A includes the compensation data generation unit 110A and the image quality control unit 130A with reference to FIG. 1, while the control device 10B includes a compensation data generation unit 110B and an image quality control unit 130B with reference to FIG. 13. The other components are substantially identical between the first embodiment of the present disclosure and the second embodiment of the present disclosure. Thus, in the second embodiment of the present disclosure, the compensation data generation unit 110B and the image quality control unit 130B will be mainly described. The image quality control unit 130B includes a compensation processing unit 150B.

2.2. Functional Configuration Example

Also in the second embodiment of the present disclosure, a technology that can reduce image quality degradation of an image captured by a variable-field-of-view endoscopic device will be mainly proposed. More specifically, as described also in the first embodiment of the present disclosure, the image quality may be degraded depending on the bent angle and rotation angle. The second embodiment of the present disclosure mainly proposes a technology of reducing image quality degradation (in particular, shape distortion) that occurs depending on such a bent angle and rotation angle.

Figure 14:
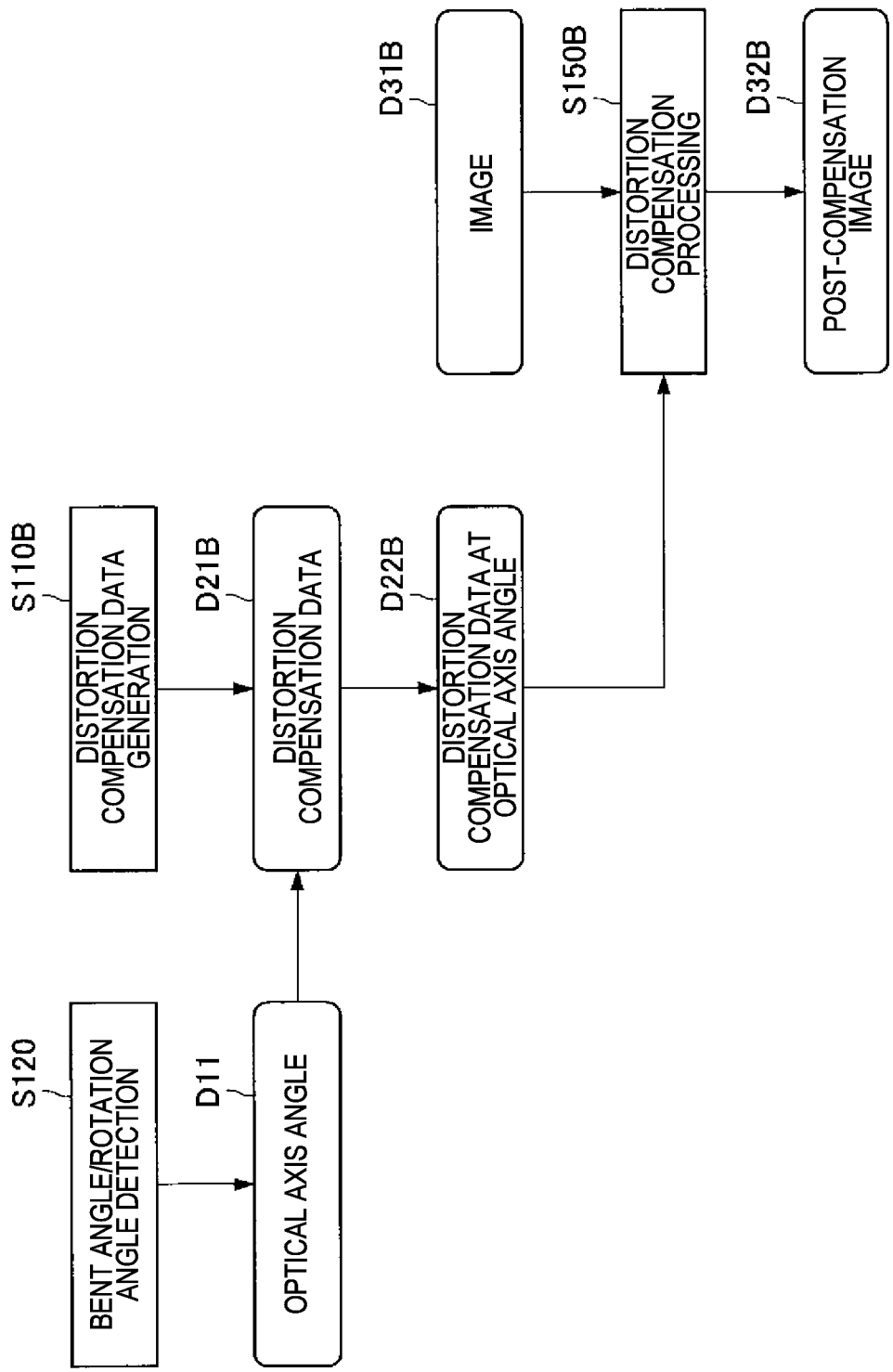
FIG. 14 is a flowchart showing an operation example of a control device according to the second embodiment of the present disclosure.

FIG. 14 is a flowchart showing an operation example of the control device 10B according to the second embodiment of the present disclosure. First, as shown in FIG. 14, the compensation data generation unit 110B (FIG. 13) generates distortion compensation data D21B in distortion compensation data generation S110B. Here, a specific example of the distortion compensation data generation S110B by the compensation data generation unit 110B will be described.

Figure 15:
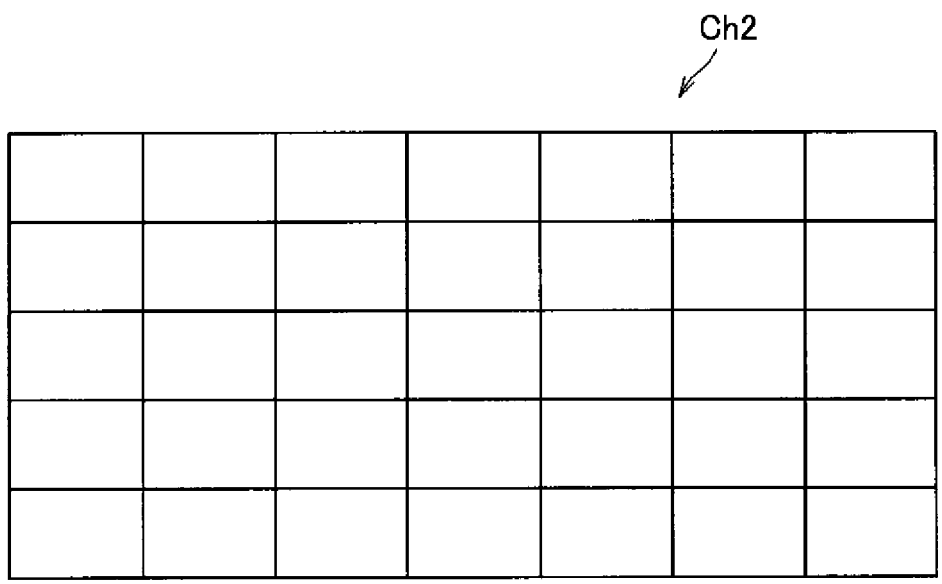
FIG. 15 is a diagram showing an example of a chart that can be utilized for generation of distortion compensation data.

FIG. 15 is a diagram showing an example of a chart that can be utilized for generation of distortion compensation data. As shown in FIG. 15, a plurality of straight lines (a plurality of straight lines drawn in a lattice) are respectively arranged vertically and horizontally in a chart Ch2 that can be utilized for generation of distortion compensation data. When such a chart Ch2 is previously imaged by the image sensor 21, a chart captured image is obtained. Imaging of the chart Ch2 may be performed similarly to the example of imaging the chart Ch1 described with reference to FIG. 7 in the first embodiment of the present disclosure.

Figure 16A:
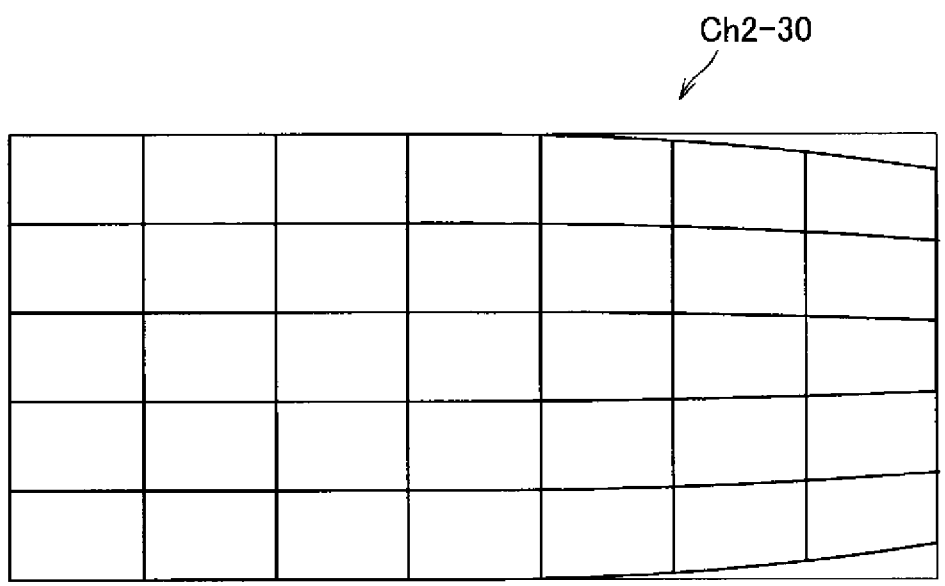
FIG. 16A is a diagram showing an example of a chart captured image obtained in the case where the bent angle (rotation angle around the Y axis) of a rigid scope is 30 degrees.
Figure 16B:
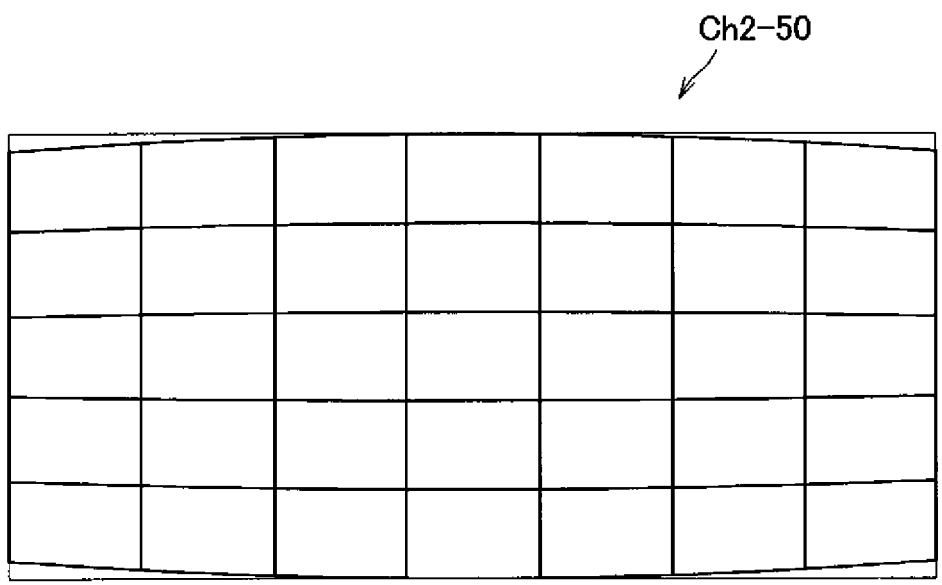
FIG. 16B is a diagram showing an example of a chart captured image obtained in the case where the bent angle (rotation angle around the Y axis) of a rigid scope is 50 degrees.
Figure 16C:
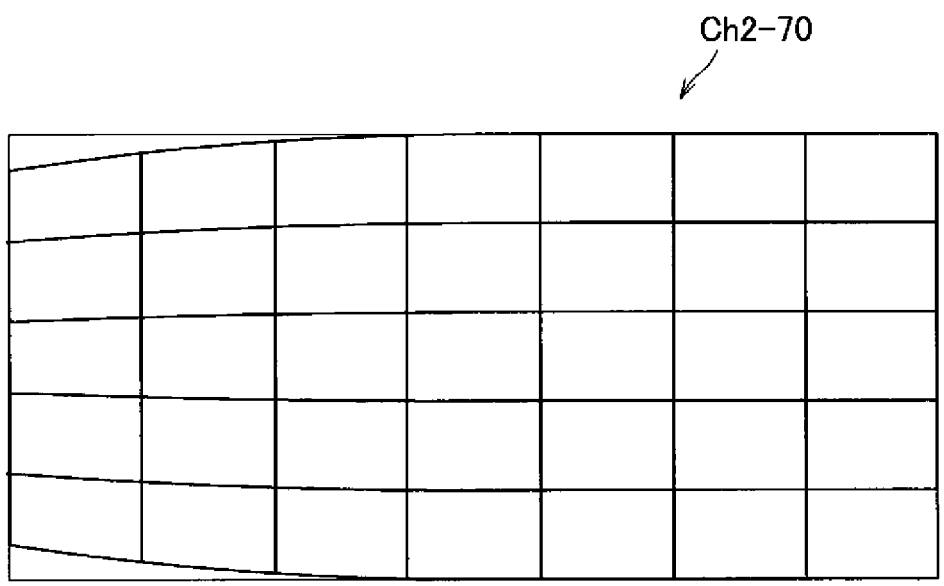
FIG. 16C is a diagram showing an example of a chart captured image obtained in the case where the bent angle (rotation angle around the Y axis) of a rigid scope is 70 degrees.

FIG. 16A is a diagram showing an example of a chart captured image Ch2-30 obtained in the case where the bent angle (the rotation angle θY around the Y axis) of the rigid scope 40 is 30 degrees. FIG. 16B is a diagram showing an example of a chart captured image Ch2-50 obtained in the case where the bent angle (the rotation angle θY around the Y axis) of the rigid scope 40 is 50 degrees. FIG. 16C is a diagram showing an example of a chart captured image Ch2-70 obtained in the case where the bent angle (the rotation angle θY around the Y axis) of the rigid scope 40 is 70 degrees. With reference to the chart captured image Ch2-30, the chart captured image Ch2-50, and the chart captured image Ch2-70, it is understood that distortion changes in accordance with a change in bent angle (the rotation angle θY around the Y axis).

Note that the examples of capturing a plurality of images of the chart Ch2 while changing the bent angle (the rotation angle θY around the Y axis) have been representatively described in FIG. 15 and FIG. 16A to FIG. 16C, whilst an angle to be changed is not only the bent angle (the rotation angle θY around the Y axis). That is, with a technique similar to the technique described with reference to FIG. 15 and FIG. 16A to FIG. 16C, a plurality of images of the chart Ch2 are captured while changing the bent angle (the rotation angle θX around the X axis), and a plurality of images of the chart Ch2 are captured while changing the rotation angle (the rotation angle θZ around the Z axis).

Figure 17A:
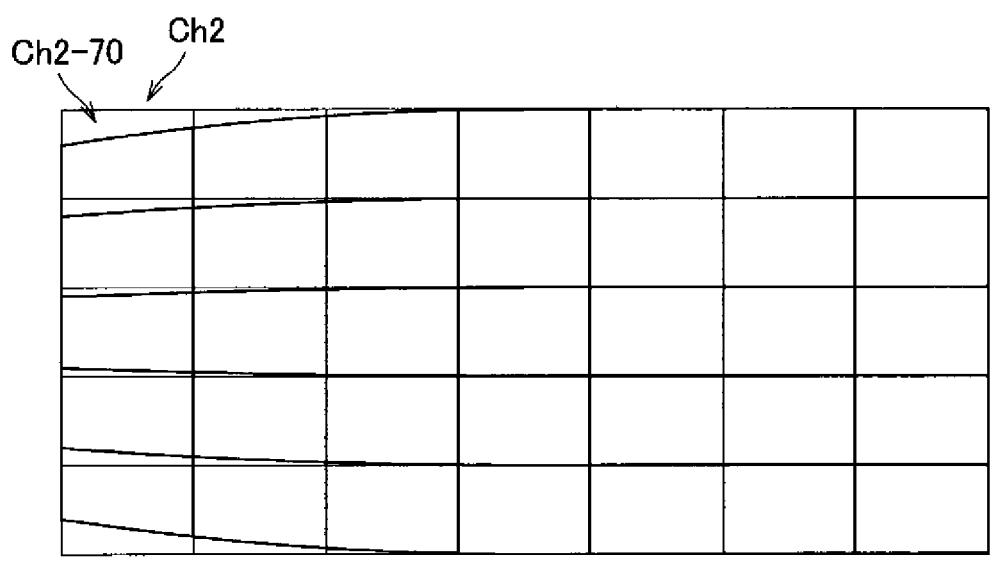
FIG. 17A is a diagram illustrating a chart and a chart captured image obtained in the case where the bent angle (rotation angle around the Y axis) is 70 degrees in an overlapping manner.

The compensation data generation unit 110B generates distortion compensation data on the basis of a chart captured image. The technique for generating distortion compensation data is not limited. Here, an example of the technique for generating distortion compensation data will be described. FIG. 17A is a diagram illustrating the chart Ch2 and the chart captured image Ch2-70 obtained in the case where the bent angle (the rotation angle θY around the Y axis) is 70 degrees in an overlapping manner. It is understood that the chart captured image Ch2-70 is distorted with respect to the chart Ch2. In addition, FIG. 17B is a diagram illustrating part of FIG. 17A in an enlarged manner.

Figure 17B:
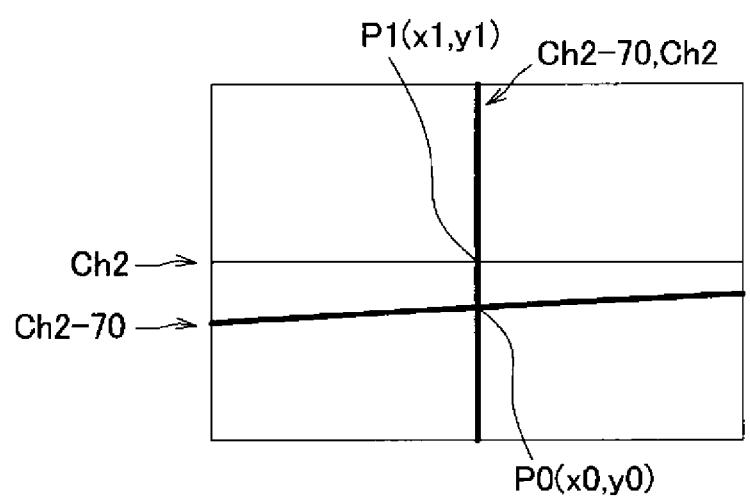
FIG. 17B is a diagram illustrating part of FIG. 17A in an enlarged manner.

With reference to FIG. 17B, a lattice point P1 (x1, y1) on the chart Ch2 has been displaced to a lattice point P0 (x0, y0) on the chart captured image Ch2-70. Therefore, the lattice point P0 (x0, y0) should be compensated to the lattice point P1 (x1, y1), and thus, the compensation data generation unit 110B calculates a compensation ratio CRx with respect to the x-coordinate of the lattice point P0 (x0, y0) as (x1/x0), and calculates a compensation ratio CRy with respect to the y-coordinate of the lattice point P0 (x0, y0) as (y1/y0). Hereinafter, the compensation ratios (CRx, CRy) with respect to the lattice point P0 may simply be referred to as a compensation ratio CR.

Figure 18:
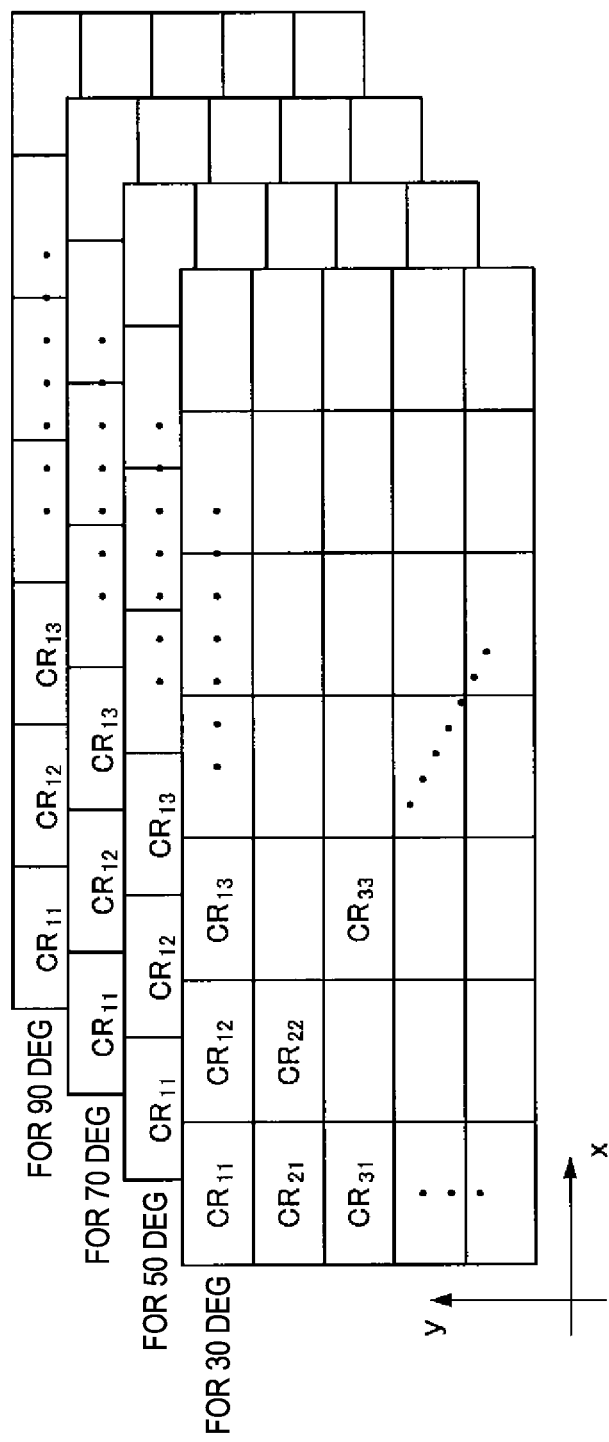
FIG. 18 is a diagram showing an example of distortion compensation data.

In this manner, the compensation data generation unit 110B is capable of calculating the compensation ratio CR for all the lattice points in the case where the bent angle (the rotation angle θY around the Y axis) is 70 degrees. The compensation data generation unit 110B is capable of obtaining the compensation ratio CR as distortion compensation data. FIG. 18 is a diagram showing an example of distortion compensation data. With reference to FIG. 18, the compensation ratio CR is shown per lattice point in each of the cases where the bent angle (the rotation angle θY around the Y axis) is 30 degrees, 50 degrees, 70 degrees, and 90 degrees.

Note that the example in which the bent angle (the rotation angle θX around the X axis) and the rotation angle (the rotation angle θZ around the Z axis) are fixed and the bent angle (the rotation angle θY around the Y axis) is changed is shown here. However, the bent angle (the rotation angle θX around the X axis) and the rotation angle (the rotation angle θZ around the Z axis) may also be changed similarly to the bent angle (the rotation angle θY around the Y axis).

Description will be continued returning to FIG. 14. Also in the second embodiment of the present disclosure, the optical axis angle (bent angle and rotation angle) D11 is detected similarly to the first embodiment of the present disclosure. Subsequently, also in the second embodiment of the present disclosure, the image quality control unit 130B controls the image quality of an image D31B captured by the image sensor 21 on the basis of the optical axis angle D11. With such a configuration, it is possible to reduce image quality degradation that occurs depending on the bent angle and the rotation angle.

For example, the image quality control unit 130B controls the image quality of the image D31B by subjecting the image D31B captured by the image sensor 21 to predetermined image processing at least based on the optical axis angle. In particular, in the second embodiment of the present disclosure, the image quality control unit 130B performs the predetermined image processing by compensating distortion of the image D31B on the basis of the optical axis angle. With such a configuration, it is possible to reduce distortion that occurs depending on the optical axis angle.

The image quality control unit 130B acquires, with the compensation processing unit 150B, data corresponding to the optical axis angle (distortion compensation data D22B at the optical axis angle) on the basis of the distortion compensation data D21B previously generated, and compensates distortion of the image D31B in distortion compensation processing S150B on the basis of the acquired data and the image D31B captured by the image sensor 21. Accordingly, a post-compensation image D32B is obtained.

Figure 19:
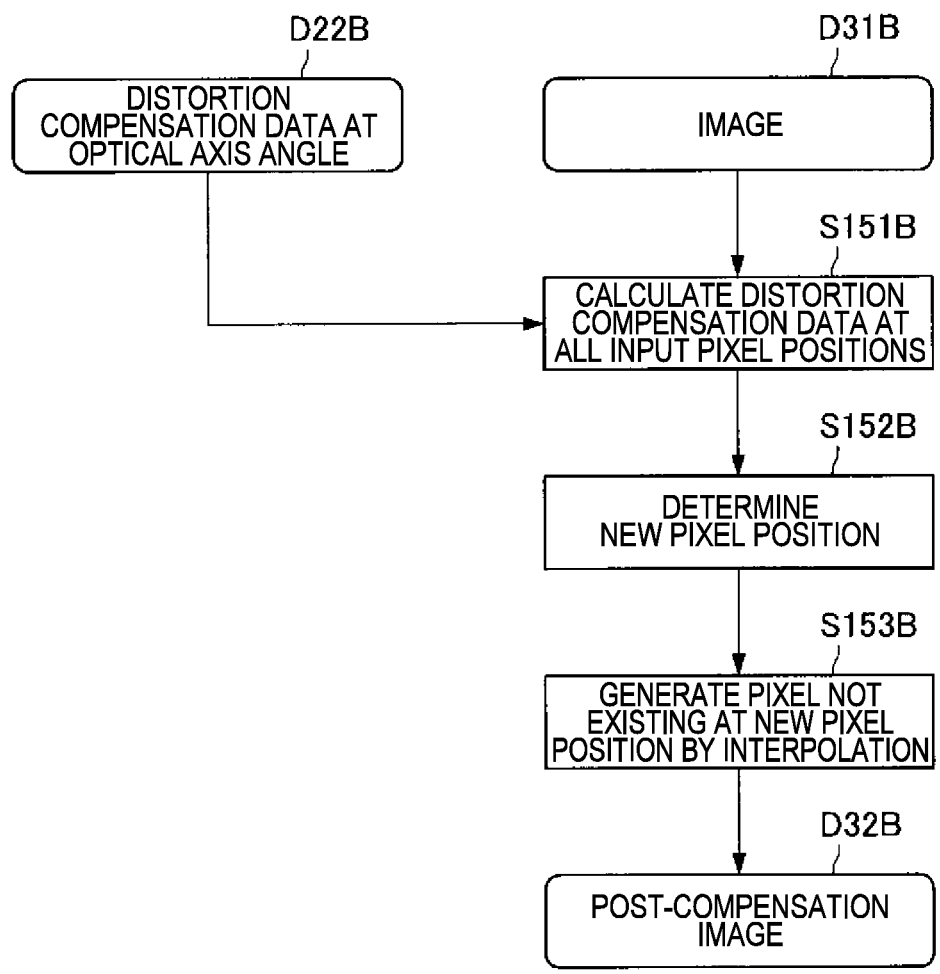
FIG. 19 is a flowchart showing a flow of a detailed operation of distortion compensation.

Description will be provided more specifically. FIG. 19 is a flowchart showing a flow of a detailed operation of distortion compensation. The image quality control unit 130B calculates, with the compensation processing unit 150B, distortion compensation data at all the pixel positions (all the input pixel positions) in the image D31B captured by the image sensor 21 on the basis of the distortion compensation data D22B (FIG. 18) at the optical axis angle (S151B). Note that, since distortion compensation data exists discretely in space, data not existing directly as distortion compensation data is obtained from directly existing distortion compensation data by interpolation or extrapolation.

Subsequently, the image quality control unit 130B determines a new pixel position (S152B) by multiplying, with the compensation processing unit 150B, each of all the input pixel positions by the compensation ratio CR corresponding to the pixel position (FIG. 18). At this time, the image quality control unit 130B generates, with the compensation processing unit 150B, a pixel not existing at the new pixel position by interpolation (S153B). Distortion is reduced from the post-compensation image D32B generated in this manner.

2.3. Variants

Figure 20A:
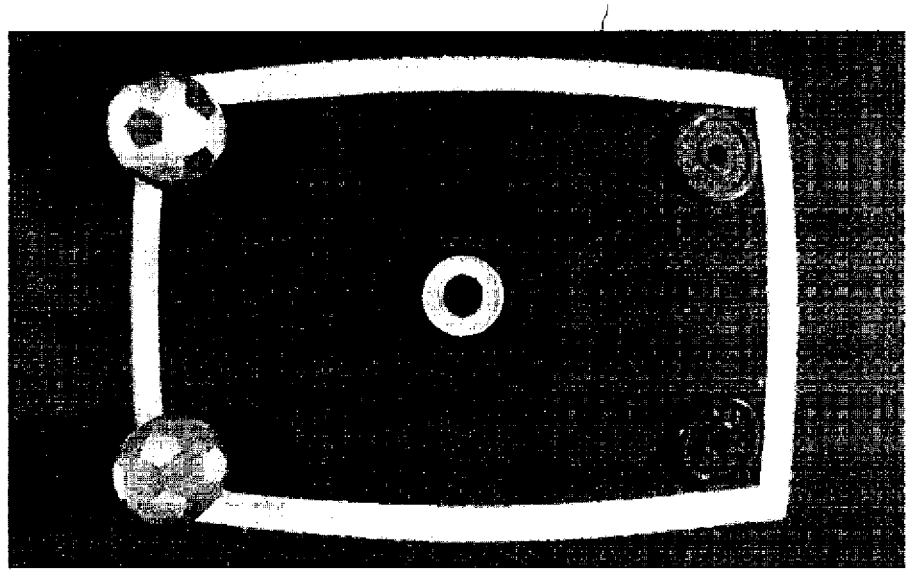
FIG. 20A is a diagram showing an example of a post-compensation image obtained by wide-angle distortion compensation.
Figure 20B:
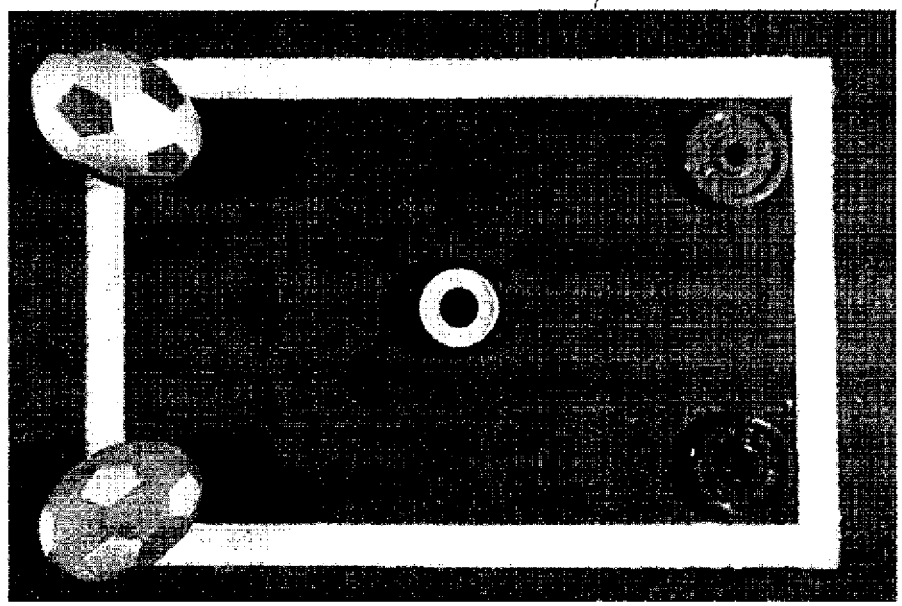
FIG. 20B is a diagram showing an example of a post-compensation image obtained by distortion compensation.

Various variants may be applied to the second embodiment of the present disclosure. For example, the example of compensation (so-called distortion compensation) of distortion occurred on straight lines has been shown above. However, depending on the application, wide-angle distortion compensation paying attention to distortion of a solid object is more suitable in some cases. FIG. 20A is a diagram showing an example of a post-compensation image D32B-1 obtained by wide-angle distortion compensation. In addition, FIG. 20B is a diagram showing an example of a post-compensation image D32B-2 obtained by distortion compensation. Distortion compensation stated here is the general term of all of form compensation methods, and distortion compensation and wide-angle distortion compensation are not compatible theoretically; however, it is also possible to mix the both at a moderate ratio in some cases to carry out the second embodiment of the present disclosure.

In addition, the example of capturing a plurality of images of a chart while moving the chart of planar shape has been described above. However, the shape of the chart is not limited to the planar shape, similarly to the first embodiment of the present disclosure. For example, the shape of the chart may be a curved surface shape. For example, as shown in FIG. 11, the chart Ch1 may have a curved surface shape. At this time, as shown in FIG. 11, the chart Ch1 having a curved surface shape may be placed along a position away from the rigid scope 40 by the distance WD frequently used for imaging.

In addition, the example in which the chart placed at a position away from the rigid scope 40 by the distance WD frequently used for imaging is imaged has been described above. However, the position at which the chart is placed is not limited to the position away from the rigid scope 40 by the distance WD frequently used for imaging, similarly to the first embodiment of the present disclosure. For example, the compensation data generation unit 110B may associate the distance from the rigid scope 40 when imaging the chart with the optical axis angle when imaging the chart and distortion compensation data.

At this time, as long as information about the distance to a subject (a depth map of a so-called imaging scene) can be acquired as described above, the image quality control unit 130B is capable of acquiring, with the compensation processing unit 150B, distance information indicating the distance to the subject, and acquiring data corresponding to the distance information and optical axis angle on the basis of distortion compensation data. If the distance information is also considered in this manner, it is expected that the accuracy of distortion compensation is improved.

Figure 21A:
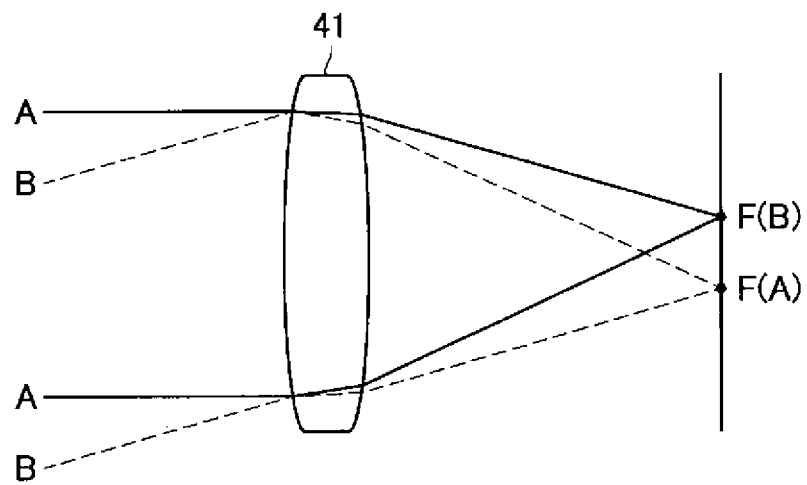
FIG. 21A is a diagram showing an example of an optical path per wavelength.

In addition, the case in which color imaging has been performed is not particularly considered above, whilst the case in which color imaging has been performed may be considered. FIG. 21A is a diagram showing an example of an optical path per wavelength. With reference to FIG. 21A, an optical path of light having a certain wavelength is indicated as F(A), and an optical path of light having another wavelength is indicated as F(B). In this manner, since the in-focus position on an image surface of light passed through the lens 41 is changed by the wavelength of light, spot and edge coloring due to magnification chromatic aberration may occur during color imaging.

Figure 21B:
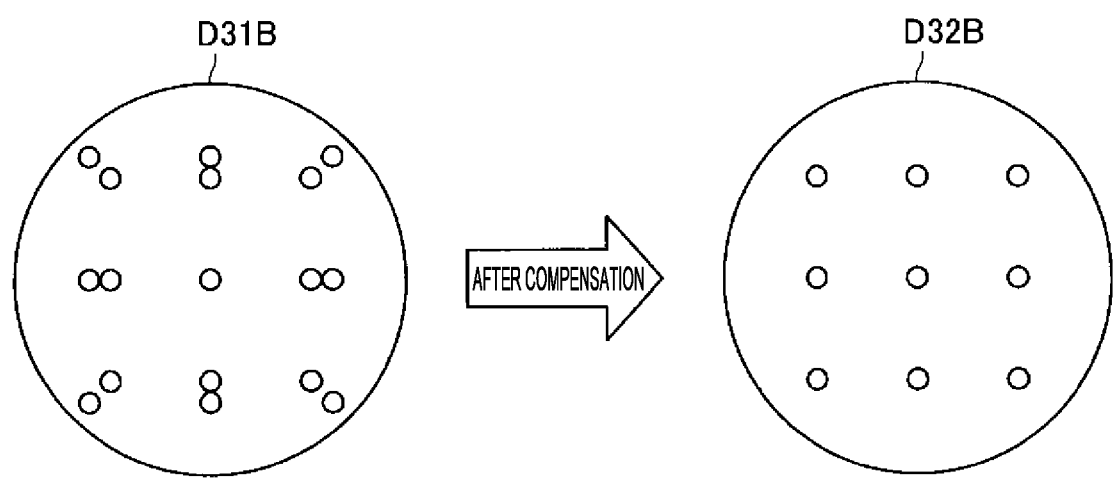
FIG. 21B is a diagram showing an example of images before and after distortion compensation is performed for all the RGB values.

Therefore, in the case where an image has RGB values, the image quality control unit 130B may perform, with the compensation processing unit 150B, image processing (in the second embodiment of the present disclosure, distortion compensation) for all the RGB values. Then, it is possible to reduce spot and edge coloring due to magnification chromatic aberration. FIG. 21B is a diagram showing an example of images before and after distortion compensation is performed for all the RGB values. With reference to FIG. 21B, it is understood that spot and edge coloring has occurred in the image D31B captured by the image sensor 21, while spot and edge coloring has been reduced in the post-compensation image D32B.

The second embodiment of the present disclosure has been described above.

3. Third Embodiment

Subsequently, a third embodiment of the present disclosure will be described.

3.1. System Configuration Example

Figure 22:
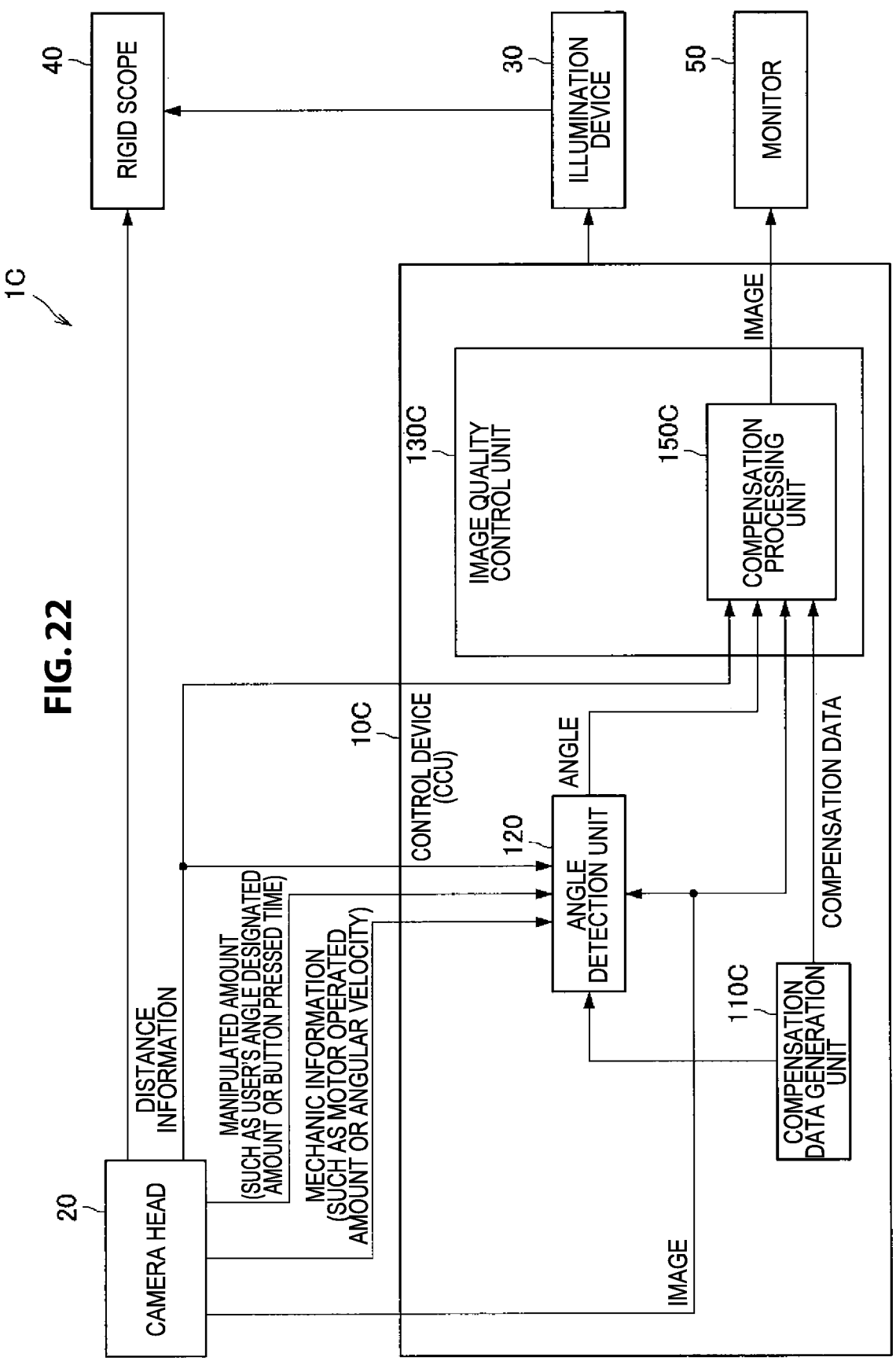
FIG. 22 is a diagram showing a configuration example of an endoscopic system according to a third embodiment of the present disclosure.

First, a configuration example of an endoscopic system according to the third embodiment of the present disclosure will be described. FIG. 22 is a diagram showing a configuration example of the endoscopic system according to the third embodiment of the present disclosure. The first embodiment of the present disclosure and the third embodiment of the present disclosure are different in that the endoscopic system 1A includes the control device 10A with reference to FIG. 1, while an endoscopic system 1C includes a control device 10C with reference to FIG. 22. The other components are substantially identical between the first embodiment of the present disclosure and the third embodiment of the present disclosure. Thus, in the third embodiment of the present disclosure, the control device 10C will be mainly described.

In addition, the first embodiment of the present disclosure and the third embodiment of the present disclosure are different in that the control device 10A includes the compensation data generation unit 110A and the image quality control unit 130A with reference to FIG. 1, while the control device 10C includes a compensation data generation unit 110C and an image quality control unit 130C with reference to FIG. 22. The other components are substantially identical between the first embodiment of the present disclosure and the third embodiment of the present disclosure. Thus, in the third embodiment of the present disclosure, the compensation data generation unit 110C and the image quality control unit 130C will be mainly described. The image quality control unit 130C includes a compensation processing unit 150C.

3.2. Functional Configuration Example

Also in the third embodiment of the present disclosure, a technology that can reduce image quality degradation of an image captured by a variable-field-of-view endoscopic device will be mainly proposed. More specifically, the optical path in the angle adjusting portion changes subtly per optical axis angle (bent angle and rotation angle), and, for example, optical axis displacement causes the manner to be affected by lens limb darkening to be changed, or a change in optical path length in the same image plane causes the amount of light passing spatially to be changed, and thus, optical luminance non-uniformity may occur. The third embodiment of the present disclosure mainly proposes a technology of reducing image quality degradation that occurs depending on such a bent angle and rotation angle (in particular, luminance non-uniformity).

Figure 23:
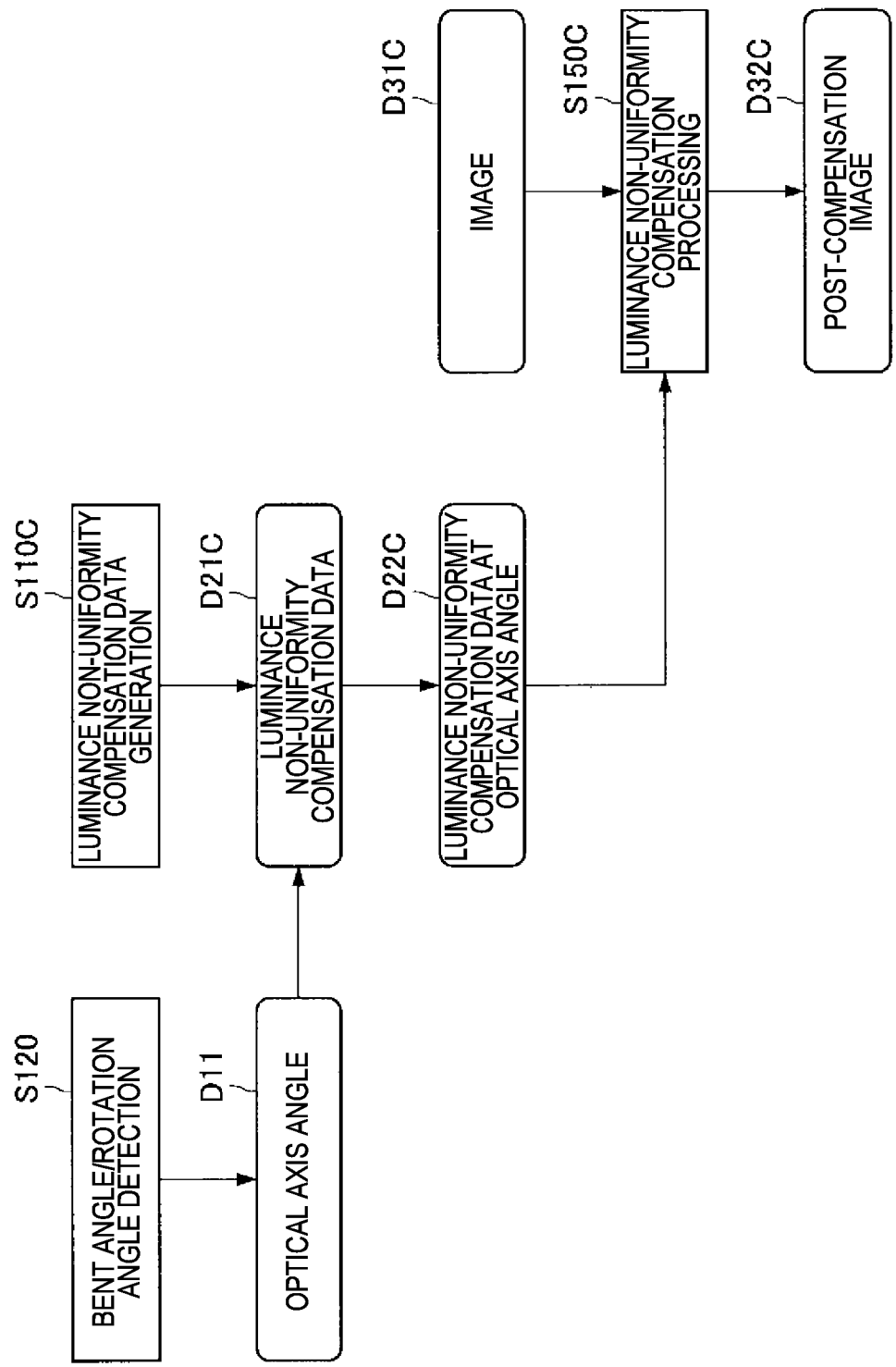
FIG. 23 is a flowchart showing an operation example of a control device according to the third embodiment of the present disclosure.

FIG. 23 is a flowchart showing an operation example of a control device 10C according to the third embodiment of the present disclosure. First, as shown in FIG. 23, the compensation data generation unit 110C (FIG. 22) generates luminance non-uniformity compensation data D21C in luminance non-uniformity compensation data generation S110C. Here, a specific example of the luminance non-uniformity compensation data generation S110C performed by the compensation data generation unit 110C will be described.

Figure 24:
FIG. 24 is a diagram showing an example of a chart that can be utilized for generation of luminance non-uniformity compensation data.

FIG. 24 is a diagram showing an example of a chart that can be utilized for generation of luminance non-uniformity compensation data. As shown in FIG. 24, a chart Ch3 that can be utilized for generation of luminance non-uniformity compensation data has such a surface (such as an 18% gray surface, for example) in which spectral reflectance becomes uniform in the whole wavelength range. When such a chart Ch3 is imaged previously by the image sensor 21, a chart captured image is obtained. Imaging of the chart Ch3 may be performed similarly to the example of imaging the chart Ch1 described with reference to FIG. 7 in the first embodiment of the present disclosure.

Figure 25A:
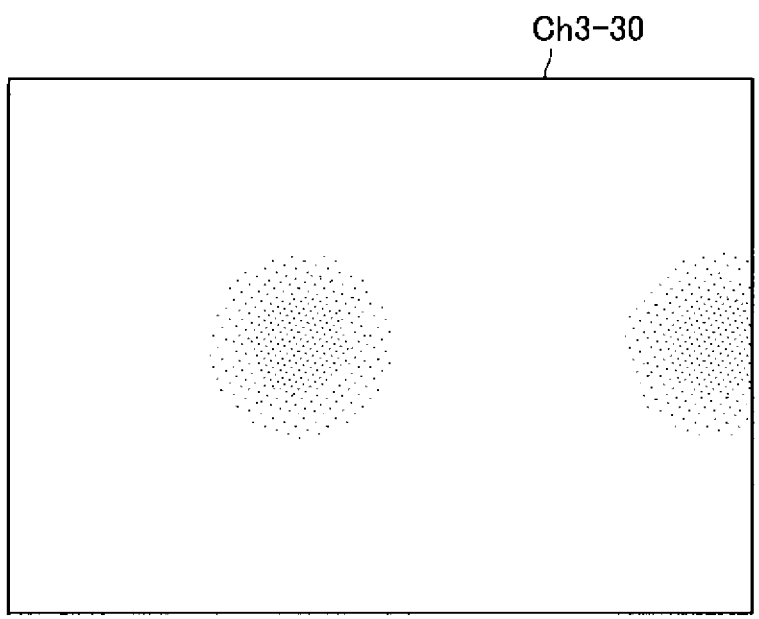
FIG. 25A is a diagram showing an example of a chart captured image obtained in the case where the bent angle (rotation angle around the Y axis) of a rigid scope is 30 degrees.
Figure 25B:
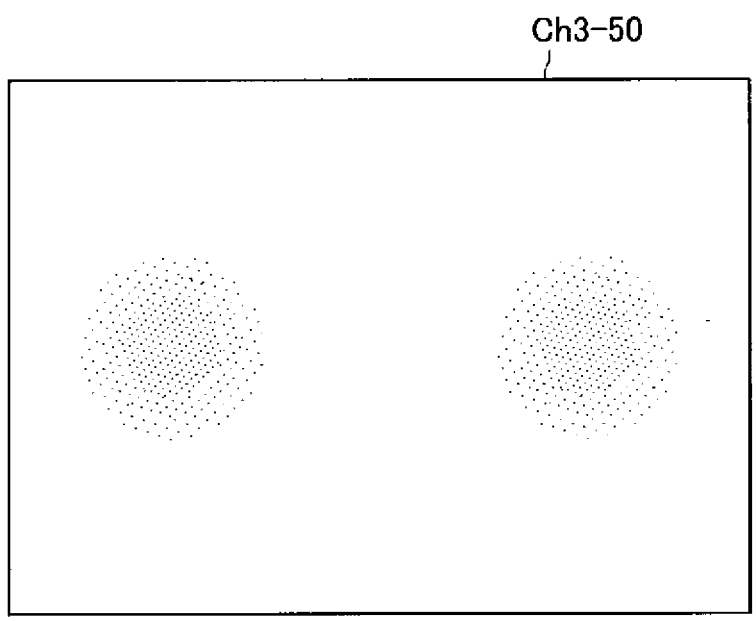
FIG. 25B is a diagram showing an example of a chart captured image obtained in the case where the bent angle (rotation angle around the Y axis) of a rigid scope is 50 degrees.
Figure 25C:
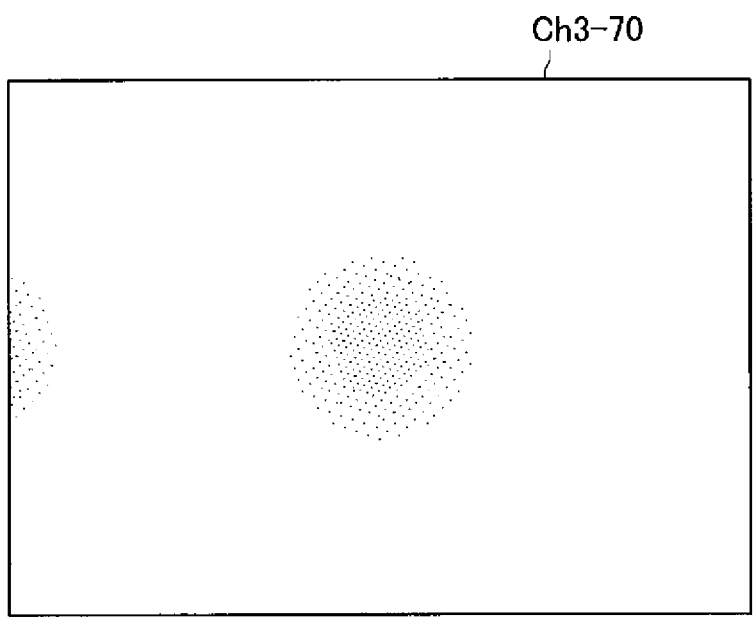
FIG. 25C is a diagram showing an example of a chart captured image obtained in the case where the bent angle (rotation angle around the Y axis) of a rigid scope is 70 degrees.

FIG. 25A is a diagram showing an example of a chart captured image Ch3-30 obtained in the case where the bent angle (the rotation angle θY around the Y axis) of the rigid scope 40 is 30 degrees. FIG. 25B is a diagram showing an example of a chart captured image Ch3-50 obtained in the case where the bent angle (the rotation angle θY around the Y axis) of the rigid scope 40 is 50 degrees. FIG. 25C is a diagram showing an example of a chart captured image Ch3-70 obtained in the case where the bent angle (the rotation angle θY around the Y axis) of the rigid scope 40 is 70 degrees. With reference to the chart captured image Ch3-30, the chart captured image Ch3-50, and the chart captured image Ch3-70, it is understood that luminance non-uniformity changes in accordance with a change in bent angle (the rotation angle θY around the Y axis).

Note that the examples of capturing a plurality of images of the chart Ch3 while changing the bent angle (the rotation angle θY around the Y axis) have been representatively described in FIG. 24 and FIG. 25A to FIG. 25C, whilst an angle to be changed is not only the bent angle (the rotation angle θY around the Y axis). That is, with a technique similar to the technique described with reference to FIG. 24 and FIG. 25A to FIG. 25C, a plurality of images of the chart Ch3 are captured while changing the bent angle (the rotation angle θX around the X axis), and a plurality of images of the chart Ch3 are captured while changing the rotation angle (the rotation angle θZ around the Z axis).

The compensation data generation unit 110C generates luminance non-uniformity compensation data on the basis of a chart captured image. The technique for generating luminance non-uniformity compensation data is not limited.

Figure 26:
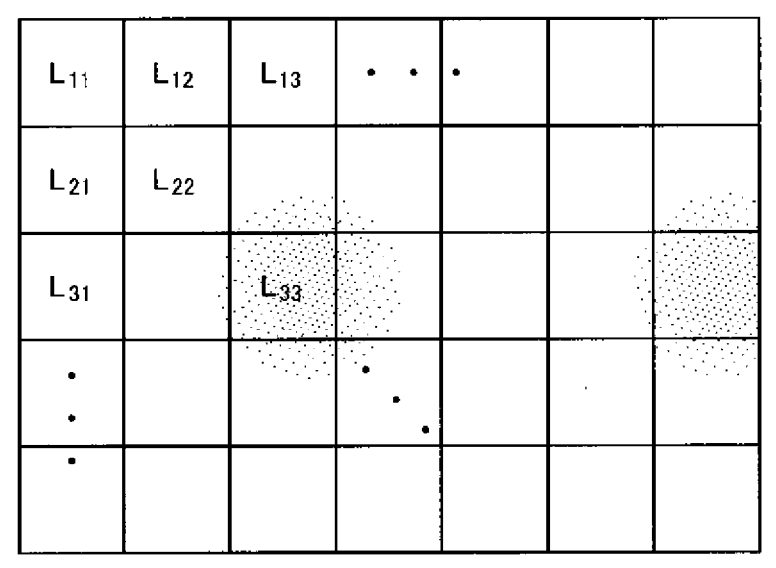

Here, an example of the technique for generating luminance non-uniformity compensation data will be described. FIG. 26 is a diagram for describing an example of the technique for generating luminance non-uniformity compensation data. As shown in FIG. 26, a plurality of spaces (hereinafter also referred to as "divided cells") obtained by dividing an imaging scene of the chart captured image Ch3-30 obtained in the case where the bent angle (the rotation angle θY around the Y axis) of the rigid scope 40 is 30 degrees are assumed.

Here, the compensation data generation unit 110C calculates average luminance Lxy of the respective divided cells. Further, the compensation data generation unit 110C calculates the average luminance of the screen. Specifically, the compensation data generation unit 110C is capable of calculating the average luminance of the screen by average luminance Lmean of the average luminance Lxy of all the divided cells in the screen, as indicated in (Formula 6) below.

[Math. 6]

$$L_{mean} = \frac{\sum_x \sum_y L_{xy}}{\text{the number of divided cells}} \quad \text{(Formula 6)}$$

Here, the amount of luminance non-uniformity is defined by a difference between the average luminance Lxy of the respective divided cells and the average luminance Lmean in the screen. In addition, a compensation ratio CLxy in each of the divided cells is defined as indicated in (Formula 7) below. The compensation data generation unit 110C generates luminance non-uniformity compensation data by calculating the compensation ratio CLxy in each of the divided cells.

[Math. 7]

$$CL_{xy} = \frac{L_{mean}}{L_{xy}} \quad \text{(Formula 7)}$$

Figure 27:
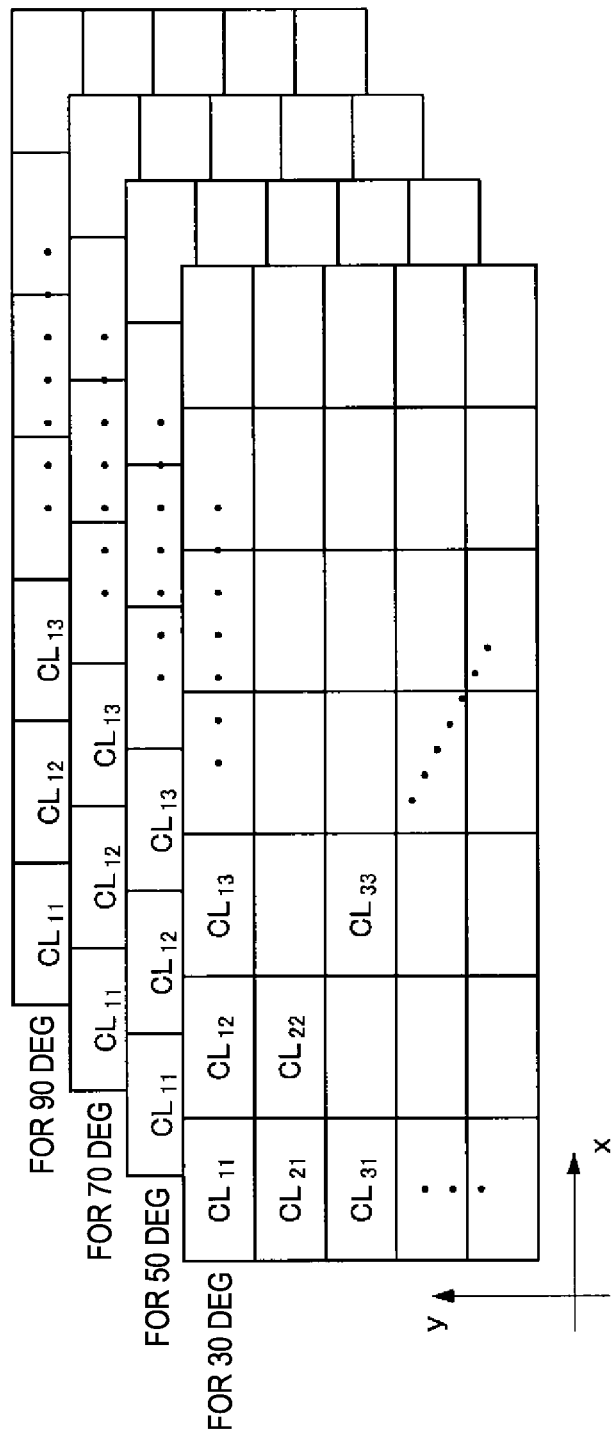
FIG. 27 is a diagram showing an example of luminance non-uniformity compensation data.

In this manner, the compensation data generation unit 110C is capable of calculating the compensation ratio CLxy for all the divided cells in the case where the bent angle (the rotation angle θY around the Y axis) is 30 degrees. The compensation data generation unit 110B is capable of obtaining the compensation ratio CLxy as luminance non-uniformity compensation data. FIG. 27 is a diagram showing an example of luminance non-uniformity compensation data. With reference to FIG. 27, the compensation ratio CLxy is shown per divided cell in each of the cases where the bent angle (the rotation angle θY around the Y axis) is 30 degrees, 50 degrees, 70 degrees, and 90 degrees.

Note that the example in which the bent angle (the rotation angle θX around the X axis) and the rotation angle (the rotation angle θZ around the Z axis) are fixed and the bent angle (the rotation angle θY around the Y axis) is changed has been shown here. However, the bent angle (the rotation angle θX around the X axis) and the rotation angle (the rotation angle θZ around the Z axis) may also be changed similarly to the bent angle (the rotation angle θY around the Y axis).

Description will be continued returning to FIG. 23. Also in the third embodiment of the present disclosure, the optical axis angle (bent angle and rotation angle) D11 is detected similarly to the first embodiment of the present disclosure. Subsequently, also in the third embodiment of the present disclosure, the image quality control unit 130C controls the image quality of an image D31C captured by the image sensor 21 on the basis of the optical axis angle D11. With such a configuration, it is possible to reduce image quality degradation that occurs depending on the bent angle and the rotation angle.

For example, the image quality control unit 130C controls the image quality of the image D31C by subjecting the image D31C captured by the image sensor 21 to predetermined image processing at least based on the optical axis angle. In particular, in the third embodiment of the present disclosure, the image quality control unit 130C performs the predetermined image processing by compensating luminance non-uniformity of the image D31C on the basis of the optical axis angle. With such a configuration, it is possible to reduce luminance non-uniformity that occurs depending on the optical axis angle.

The image quality control unit 130C acquires, with the compensation processing unit 150C, data (luminance non-uniformity compensation data D22C at the optical axis angle) corresponding to the optical axis angle on the basis of the luminance non-uniformity compensation data D21C previously generated, and compensates luminance non-uniformity of the image D31C in luminance non-uniformity compensation processing S150C on the basis of the acquired data and the image D31C captured by the image sensor 21. Accordingly, a post-compensation image D32C is obtained.

More specifically, the image quality control unit 130C compensates luminance non-uniformity by multiplying, with the compensation processing unit 150C, the image D31C captured by the image sensor 21 and luminance non-uniformity compensation data as shown in FIG. 27. Accordingly, an image obtained by imaging such a surface that spectral reflectance becomes uniform has uniform luminance, and luminance non-uniformity is compensated.

3.3. Variants

Various variants may be applied to the third embodiment of the present disclosure. For example, an example of the technique for compensating luminance non-uniformity has been described above, whilst the technique for compensating luminance non-uniformity is not particularly limited. In addition, the definition of luminance is also not particularly limited. For example, for luminance, the definition of luminance may also be Y of YCbCr, L of CIELAB, or another signal, for example. In addition, the example of performing compensation such that luminance in the screen agrees with the average luminance has been described above, whilst compensation may be performed such that luminance in the screen agrees with predetermined reference luminance different from the average luminance.

In addition, the example of capturing a plurality of images of a chart while moving the chart of planar shape has been described above. However, similarly to the first embodiment of the present disclosure, the shape of the chart is not limited to the planar shape. For example, the shape of the chart may be a curved surface shape. For example, as shown in FIG. 11, the chart Ch1 may have a curved surface shape. At this time, as shown in FIG. 11, the chart Ch1 having a curved surface shape may be placed along a position away from the rigid scope 40 by the distance WD frequently used for imaging.

In addition, the example in which the chart placed at a position away from the rigid scope 40 by the distance WD frequently used for imaging is imaged has been described above. However, similarly to the first embodiment of the present disclosure, the position at which the chart is placed is not limited to the position away from the rigid scope 40 by the distance WD frequently used for imaging. For example, the compensation data generation unit 110C may associate the distance from the rigid scope 40 when imaging the chart with the optical axis angle when imaging the chart and luminance non-uniformity compensation data.

At this time, as long as information about the distance to a subject (a depth map of a so-called imaging scene) can be acquired as described above, the image quality control unit 130C is capable of acquiring, with the compensation processing unit 150C, distance information indicating the distance to the subject, and acquiring data corresponding to the distance information and optical axis angle on the basis of luminance non-uniformity compensation data. If the distance information is also considered in this manner, it is expected that the accuracy of luminance non-uniformity compensation is improved.

Figure 28:
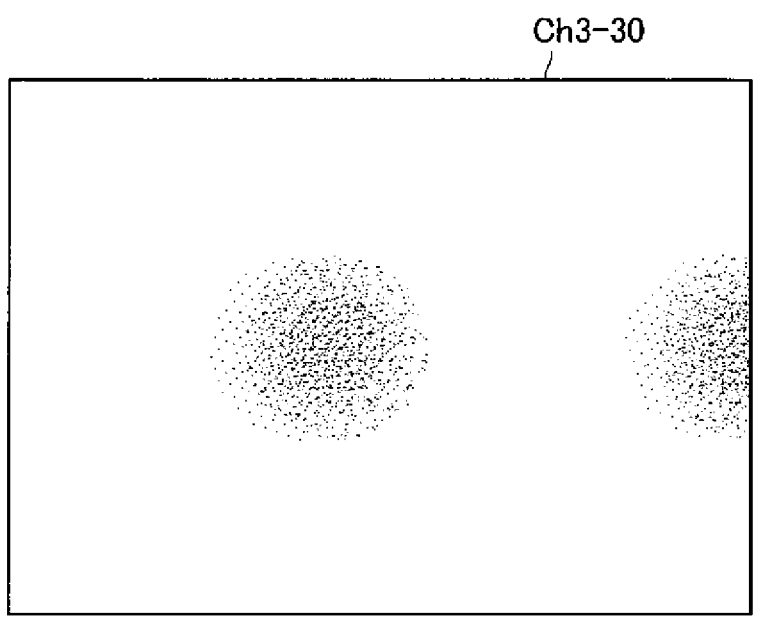
FIG. 28 is a diagram showing an example of a chart captured image obtained without considering color imaging in the case where the bent angle (rotation angle around the Y axis) of a rigid scope is 30 degrees.

In addition, the case in which color imaging has been performed is not particularly considered above, whilst the case in which color imaging has been performed may be considered. FIG. 28 is a diagram showing an example of the chart captured image Ch3-30 obtained without considering color imaging in the case where the bent angle (the rotation angle θY around the Y axis) of the rigid scope 40 is 30 degrees. With reference to FIG. 28, unnatural coloring non-uniformity has occurred in the chart captured image Ch3-30 obtained without considering color imaging.

Therefore, in the case where an image has RGB values, the image quality control unit 130C may perform, with the compensation processing unit 150C, image processing (in the third embodiment of the present disclosure, luminance non-uniformity compensation) for all the RGB values. Then, it is possible to reduce unnatural coloring non-uniformity.

The third embodiment of the present disclosure has been described above.

4. Fourth Embodiment

Subsequently, a fourth embodiment of the present disclosure will be described.

4.1. System Configuration Example

Figure 29:
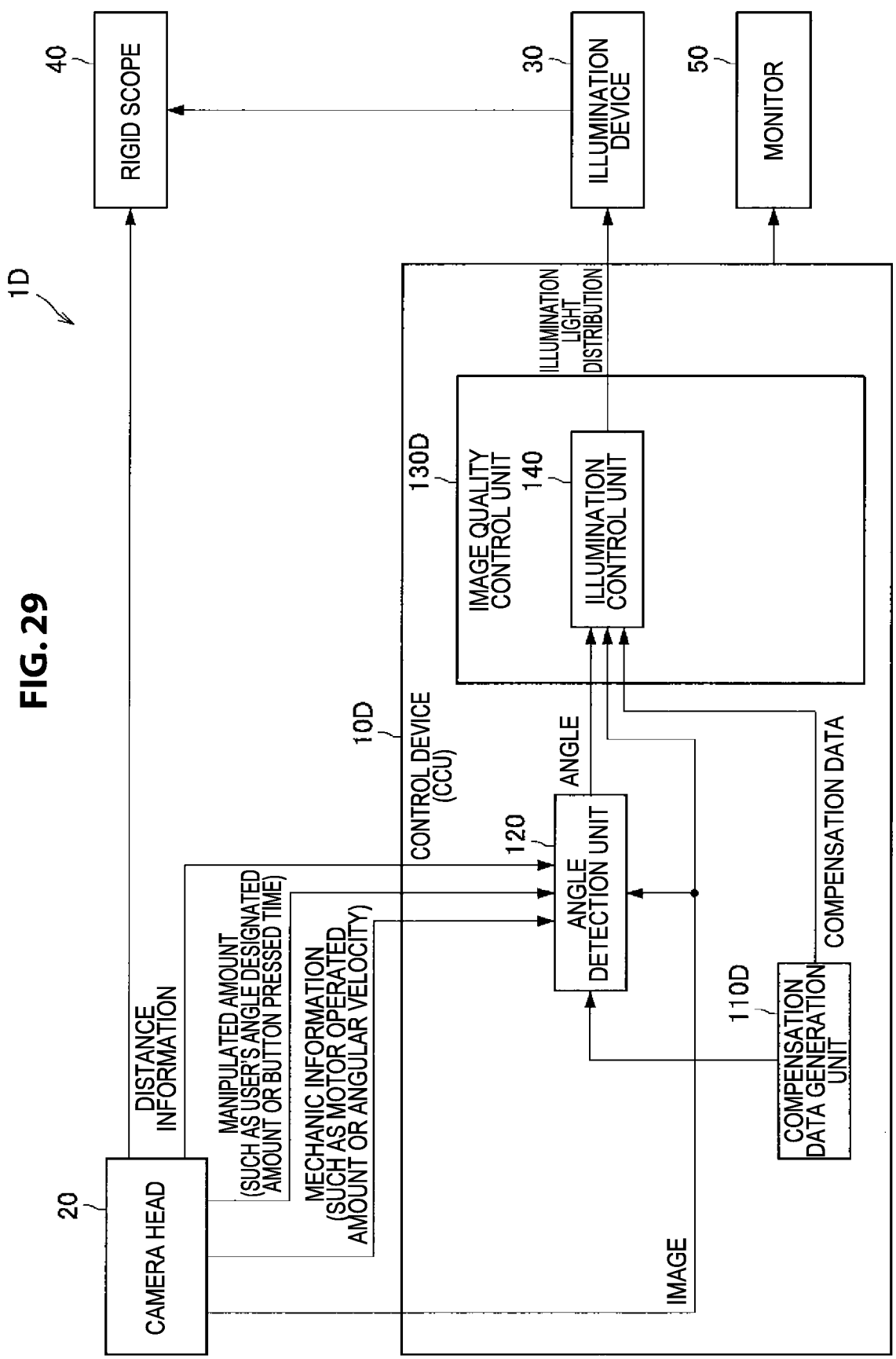
FIG. 29 is a diagram showing a configuration example of an endoscopic system according to a fourth embodiment of the present disclosure.

First, a configuration example of an endoscopic system according to the fourth embodiment of the present disclosure will be described. FIG. 29 is a diagram showing a configuration example of the endoscopic system according to the fourth embodiment of the present disclosure. The first embodiment of the present disclosure and the fourth embodiment of the present disclosure are different in that the endoscopic system 1A includes the control device 10A with reference to FIG. 1, while an endoscopic system 1D includes a control device 10D with reference to FIG. 29. The other components are substantially identical between the first embodiment of the present disclosure and the fourth embodiment of the present disclosure (as described above, except that the light source angle of the illumination device 30 is variable in the fourth embodiment of the present disclosure). Thus, in the fourth embodiment of the present disclosure, the control device 10D will be mainly described.

In addition, the first embodiment of the present disclosure and the fourth embodiment of the present disclosure are different in that the control device 10A includes the compensation data generation unit 110A and the image quality control unit 130A with reference to FIG. 1, while the control device 10D includes a compensation data generation unit 110D and an image quality control unit 130D with reference to FIG. 29. The other components are substantially identical between the first embodiment of the present disclosure and the fourth embodiment of the present disclosure. Thus, in the fourth embodiment of the present disclosure, the compensation data generation unit 110D and the image quality control unit 130D will be mainly described. The image quality control unit 130D includes an illumination control unit 140.

4.2. Functional Configuration Example

Also in the fourth embodiment of the present disclosure, a technology that can reduce image quality degradation of an image captured by a variable-field-of-view endoscopic device will be mainly proposed. More specifically, since the manner in which light emitted from the illumination device 30 is applied to a subject changes in association with a change in optical axis angle (bent angle and rotation angle), light distribution non-uniformity may occur. The fourth embodiment of the present disclosure mainly proposes a technology of reducing image quality degradation (in particular, light distribution non-uniformity) that occurs depending on such a bent angle and rotation angle.

Figure 30:
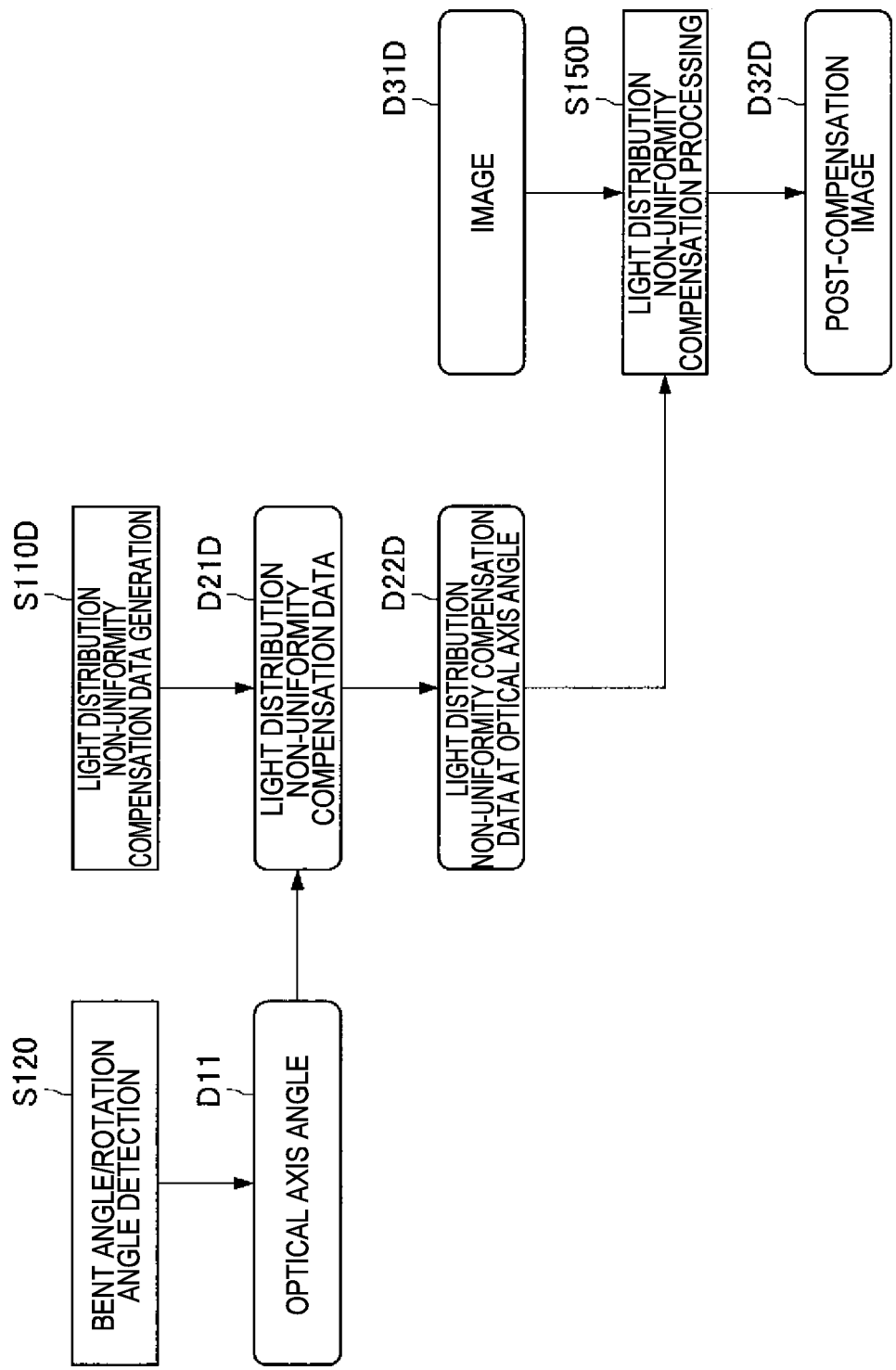
FIG. 30 is a flowchart showing an operation example of a control device according to the fourth embodiment of the present disclosure.
Figure 31A:
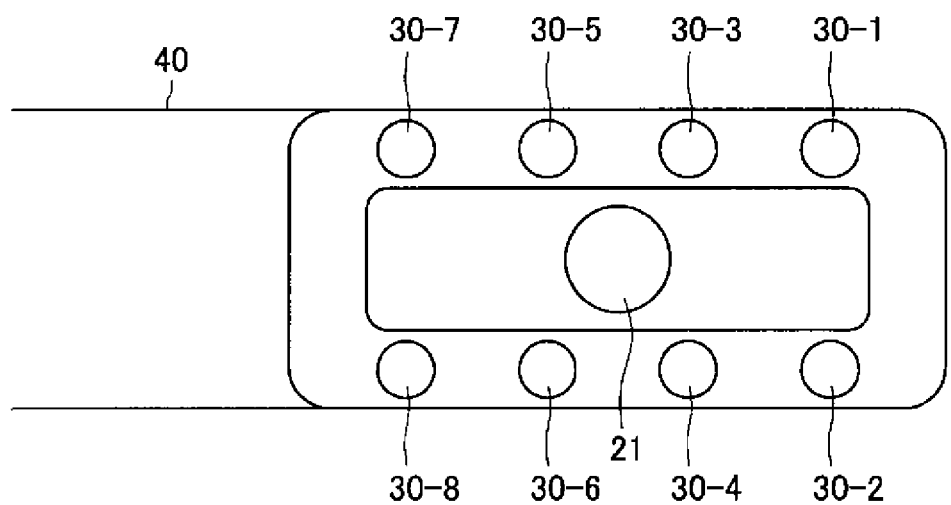
FIG. 31A is a diagram showing an example of light sources whose angles are variable.

FIG. 30 is a flowchart showing an operation example of the control device 10D according to the fourth embodiment of the present disclosure. As described above, in the fourth embodiment of the present disclosure, the light source angle of the illumination device 30 is variable. First, the illumination device 30 whose light source angle is variable will be described. FIG. 31A is a diagram showing an example of light sources whose angles are variable. As shown in FIG. 31A, light sources 30-1 to 30-8 whose angles are variable are provided on the leading end of the rigid scope 40. Note that the number of light sources is eight in the example shown in FIG. 31A, whilst the number of light sources is not particularly limited.

Figure 31B:
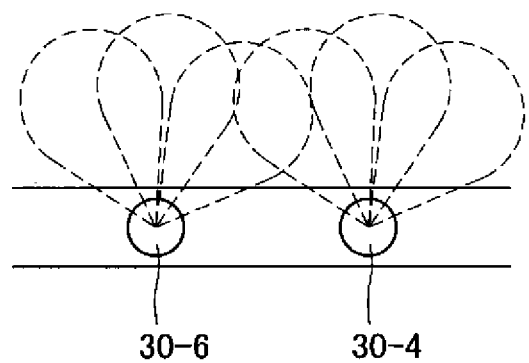
FIG. 31B is a diagram showing the manner in which light emitted from the light sources changes in orientation in association with a change in light source angle.

In addition, FIG. 31B is a diagram showing the manner in which light emitted from the light sources changes in orientation in association with a change in light source angle. As shown in FIG. 31B, light emitted from the light source 30-4 whose angle is variable changes in orientation in association with a change in angle of the light source 30-4. Similarly, light emitted from the light source 30-6 whose angle is variable changes in orientation in association with a change in angle of the light source 30-6. Note that the light sources 30-4 and 30-6 are shown as representatives in FIG. 31B, whilst, in the other light sources (the light sources 30-1 to 30-3, 30-5, 30-7, and 30-8), light emitted from the light sources similarly changes in orientation in association with a change in angle.

Returning to FIG. 30, description of the operation of the control device 10D will be continued. As shown in FIG. 30, the compensation data generation unit 110D (FIG. 29) generates the light distribution non-uniformity compensation data D21D in light distribution non-uniformity compensation data generation S110D. Here, a specific example of the light distribution non-uniformity compensation data generation S110D by the compensation data generation unit 110D will be described.

In the fourth embodiment of the present disclosure, a chart similar to the chart (FIG. 24) that can be utilized for generation of luminance non-uniformity compensation data in the third embodiment of the present disclosure can be utilized for generation of light distribution non-uniformity compensation data. Also in the fourth embodiment of the present disclosure, when such a chart Ch3 (FIG. 24) is imaged previously by the image sensor 21, a chart captured image is obtained. Imaging of the chart Ch3 may be performed similarly to the example of imaging the chart Ch1 described with reference to FIG. 7 in the first embodiment of the present disclosure.

At this time, with reference to the chart captured images described in the third embodiment of the present disclosure (with reference to the chart captured image Ch3-30 (FIG. 25A), the chart captured image Ch3-50 (FIG. 25B), and the chart captured image Ch3-70 (FIG. 25C)), it is understood that light distribution non-uniformity changes in accordance with a change in bent angle (the rotation angle θY around the Y axis).

Note that the examples of capturing a plurality of images of the chart Ch3 while changing the bent angle (the rotation angle θY around the Y axis) have been representatively described in FIG. 24 and FIG. 25A to FIG. 25C, whilst an angle to be changed is not only the bent angle (the rotation angle θY around the Y axis). That is, with a technique similar to the technique described with reference to FIG. 24 and FIG. 25A to FIG. 25C, a plurality of images of the chart Ch3 are captured while changing the bent angle (the rotation angle θX around the X axis), and a plurality of images of the chart Ch3 are captured while changing the rotation angle (the rotation angle θZ around the Z axis).

Figure 32:
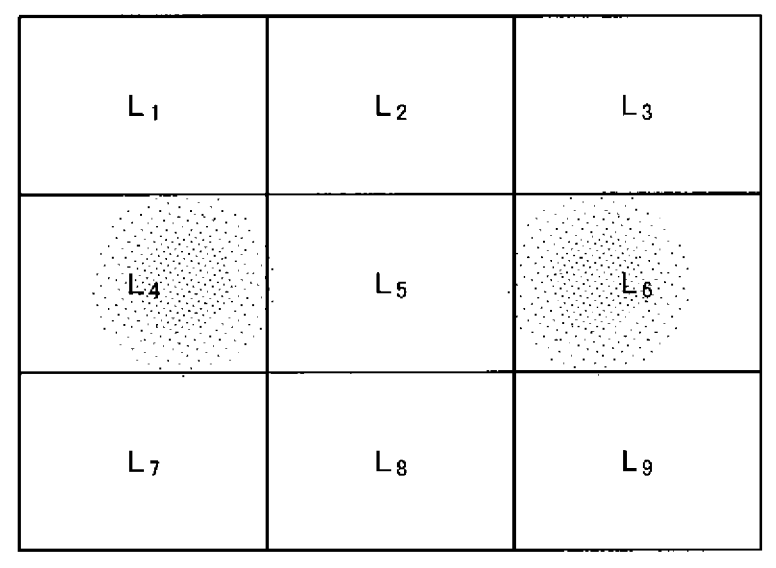

The compensation data generation unit 110D calculates a light distribution non-uniformity evaluation value per light source angle of the illumination device 30 on the basis of a chart captured image, and generates light distribution non-uniformity compensation data on the basis of the light distribution non-uniformity evaluation value. The technique for generating light distribution non-uniformity compensation data is not limited. Here, an example of the technique for generating light distribution non-uniformity compensation data will be described. FIG. 32 is a diagram for describing an example of the technique for generating light distribution non-uniformity compensation data. As shown in FIG. 32, a plurality of spaces (hereinafter also referred to as "divided cells") obtained by dividing an imaging scene of the chart captured image Ch3-30 obtained in the case where the bent angle (the rotation angle θY around the Y axis) of the rigid scope 40 is 30 degrees are assumed.

Here, the compensation data generation unit 110D calculates a light distribution non-uniformity evaluation value in accordance with standard deviation of the average luminance L of all the divided cells while changing the light source angle, as indicated in (Formula 8) below. Then, the compensation data generation unit 110D generates a light source angle at which the light distribution non-uniformity evaluation value is minimized as light distribution non-uniformity compensation data. Generation of such light distribution non-uniformity compensation data will be described in detail with reference to FIG. 33.

[Math. 8]

$$DL = \text{standard deviation of } L1 - L9 = \frac{1}{9}\sum_{k=1}^{9}(L_k - m)^2 \quad \text{(Formula 8)}$$

Figure 33:
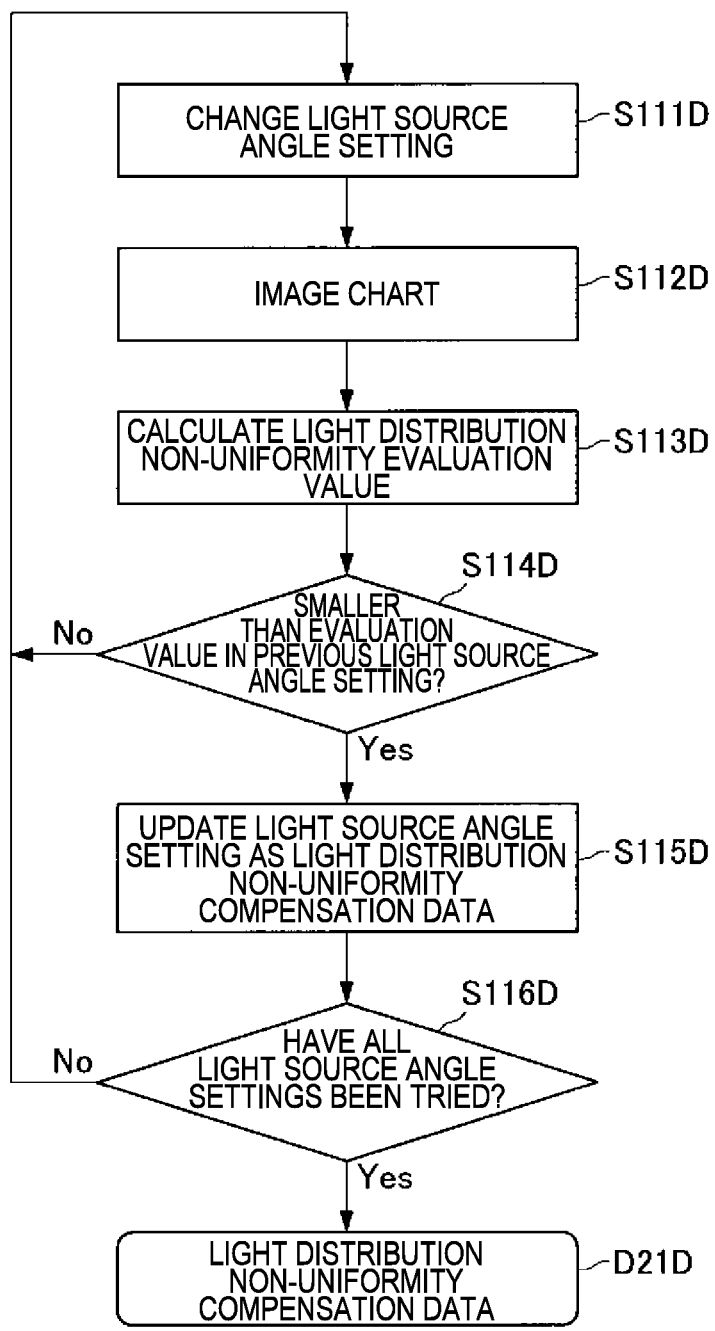
FIG. 33 is a flowchart showing a flow of an operation of generating light distribution non-uniformity compensation data.

FIG. 33 is a flowchart showing a flow of an operation of generating light distribution non-uniformity compensation data. As shown in FIG. 33, first, the compensation data generation unit 110D changes a setting of the light source angle (S111D), acquires a chart captured image at the light source angle changed in setting (S112D), and calculates a light distribution non-uniformity evaluation value (S113D).

Subsequently, in the case where the calculated light distribution non-uniformity evaluation value is not smaller than the light distribution non-uniformity evaluation value in the previous light source angle setting ("No" in S114D), the compensation data generation unit 110D transitions the operation to S110D. On the other hand, in the case where the calculated light distribution non-uniformity evaluation value is smaller than the light distribution non-uniformity evaluation value in the previous light source angle setting (alternatively, in the case where the light distribution non-uniformity evaluation value is calculated for the first time) ("Yes" in S114D), the compensation data generation unit 110D updates the light source angle setting as light distribution non-uniformity compensation data (S115D).

Subsequently, in the case where there is a light source angle setting not yet tried ("No" in S116D), the compensation data generation unit 110D transitions the operation to S110D. On the other hand, all light source angle settings have been tried ("Yes" in S116D), the compensation data generation unit 110D obtains the light distribution non-uniformity compensation data D21D after the last update in S115D.

Figure 34A:
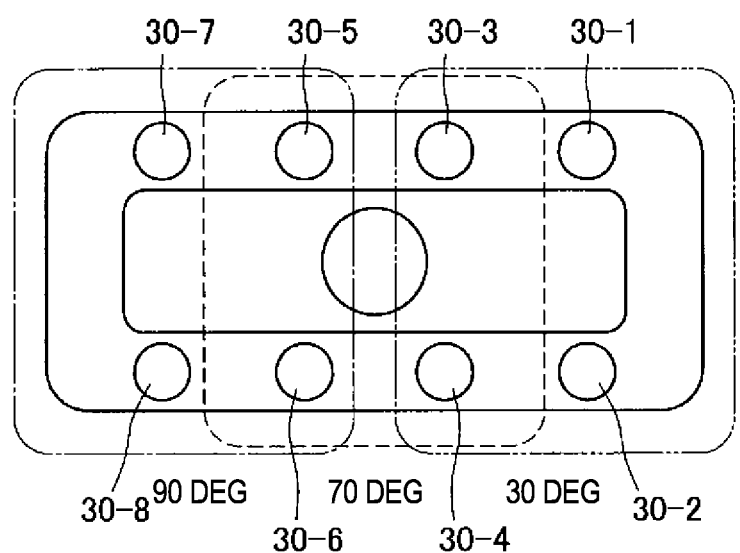
FIG. 34A is a diagram showing an example of light distribution non-uniformity compensation data.

In this manner, the compensation data generation unit 110D is capable of obtaining a light source angle at which the light distribution non-uniformity evaluation value is minimized in the case where the bent angle (the rotation angle θY around the Y axis) is 30 degrees as light distribution non-uniformity compensation data. FIG. 34A and FIG. 34B are diagrams showing an example of light distribution non-uniformity compensation data. With reference to FIG. 34A and FIG. 34B, in the case where the bent angle (the rotation angle BY around the Y axis) is 30 degrees, the angles of the light sources 30-1 to 30-4 are angles a to d different from a reference position (for example, front), while the angles of the light sources 30-1 to 30-4 are at the reference position (for example, front).

On the other hand, in the case where the bent angle (the rotation angle θY around the Y axis) is 70 degrees, the angles of the light sources 30-3 to 30-6 are angles e to h different from the reference position (for example, front), while the angles of the light sources 30-1, 30-2, 30-7, and 30-8 are at the reference position (for example, front). In addition, in the case where the bent angle (the rotation angle θY around the Y axis) is 90 degrees, the angles of the light sources 30-5 to 30-8 are angles i to l different from the reference position (for example, front), while the angles of the light sources 30-1 to 30-4 are at the reference position (for example, front).

Note that the example in which the bent angle (the rotation angle θX around the X axis) and the rotation angle (the rotation angle θZ around the Z axis) are fixed and the bent angle (the rotation angle θY around the Y axis) is changed has been shown here. However, the bent angle (the rotation angle θX around the X axis) and the rotation angle (the rotation angle θZ around the Z axis) may also be changed similarly to the bent angle (the rotation angle θY around the Y axis).

Description will be continued returning to FIG. 30. Also in the fourth embodiment of the present disclosure, the optical axis angle (bent angle and rotation angle) D11 is detected similarly to the first embodiment of the present disclosure. Subsequently, also in the fourth embodiment of the present disclosure, the image quality control unit 130D controls the image quality of an image D31D captured by the image sensor 21 on the basis of the optical axis angle D11. With such a configuration, it is possible to reduce image quality degradation that occurs depending on the bent angle and the rotation angle.

For example, the image quality control unit 130D controls the image quality of the image D31D by controlling at least the illumination device 30 on the basis of the optical axis angle. In particular, in the fourth embodiment of the present disclosure, the image quality control unit 130D controls the image quality of the image D31D by compensating light distribution non-uniformity of the image D31D by the control of the illumination device 30 based on the optical axis angle. With such a configuration, it is possible to reduce light distribution non-uniformity that occurs depending on the optical axis angle.

The image quality control unit 130D acquires, with the illumination control unit 140, data corresponding to the optical axis angle (light distribution non-uniformity compensation data D22D at the optical axis angle) on the basis of the light distribution non-uniformity compensation data D21D previously generated, and on the basis of the acquired data, compensates light distribution non-uniformity of the image D31D in light distribution non-uniformity compensation processing S150D. Accordingly, a post-compensation image D32D is obtained.

More specifically, the image quality control unit 130D acquires, with the illumination control unit 140, a light source angle corresponding to the optical axis angle on the basis of the light distribution non-uniformity compensation data D21D previously generated, and in accordance with the acquired light source angle, adjusts the angles of the light sources 30-1 to 30-8 of the illumination device 30. Accordingly, light distribution non-uniformity is reduced from a captured image of a subject illuminated with light sources whose angles have been changed.

4.3. Variants

Various variants may be applied to the fourth embodiment of the present disclosure. For example, the technique for compensating light distribution non-uniformity has been described above, whilst compensation of light distribution non-uniformity and compensation of luminance non-uniformity may be executed in combination. That is, the third embodiment of the present disclosure and the fourth embodiment of the present disclosure may be executed in combination. For example, after performing compensation of light distribution non-uniformity under control of the illumination device 30, compensation of luminance non-uniformity may be performed by image processing. Similarly, any of the first embodiment of the present disclosure to the fourth embodiment of the present disclosure described above may be executed in combination in an appropriate manner.

The fourth embodiment of the present disclosure has been described above.

2. Conclusion

As described above, according to embodiments of the present disclosure, a control device including an image quality control unit that controls the image quality of an image for display on the basis of optical axis angle information with reference to the scope axis of an endoscope and an image signal acquired by an image sensor is provided.

With such a configuration, it is possible to reduce image quality degradation of an image captured by a variable-field-of-view endoscopic device.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, the example in which image quality control in accordance with the optical axis angle is executed by the endoscopic device has been mainly described above. However, the image quality control described above may be executed by an apparatus different from the endoscopic device. For example, the image quality control described above may be executed by a microscope or the like. In addition, the case in which the image quality control described above is applied to an endoscopic device utilized in the medical field has been mainly assumed, whilst the image quality control described above may also be applied widely to every field other than the medical field.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A control device including:

an image quality control unit configured to control image quality of an image for display on a basis of optical axis angle information with reference to a scope axis of an endoscope and an image signal acquired by an image sensor.

(2)

The control device according to (1), in which the optical axis angle information is information detected by an angle detection device or information obtained by acquiring light source angle information controlled by an imaging device.

(3)

The control device according to (1) or (2), in which the image quality control unit controls image quality of the image for display on a basis of compensation data corresponding to the optical axis angle information and the image signal.

(4)

The control device according to (3), further including:

a compensation data generation unit, in which the compensation data generation unit generates the compensation data on a basis of a chart image signal obtained by imaging a predetermined chart.

(5)

The control device according to any one of (1) to (4), in which the image quality control unit controls image quality of the image for display on a basis of distance information indicating a distance to a subject, compensation data corresponding to the optical axis angle information, and the image signal.

(6)

The control device according to any one of (1) to (5), in which in a case where the image signal has an R signal, a G signal, and a B signal, the image quality control unit controls image quality of the image for display on a basis of respective image signals.

(7)

The control device according to any one of (1) to (6), in which the image quality control unit controls at least one of blur non-uniformity, distortion, or luminance non-uniformity of the image for display.

(8)

The control device according to (4), in which the compensation data generation unit estimates a point spread function that changes depending on a spatial position on a basis of the chart image signal, and generates compensation data for controlling blur non-uniformity from the point spread function.

(9)

The control device according to any one of (1) to (8), in which the image quality control unit adjusts a light source device on a basis of the optical axis angle information, and controls image quality of the image for display.

(10)

The control device according to (9), in which the image quality control unit controls light distribution non-uniformity of the image for display.

(11)

The control device according to (4), in which the compensation data generation unit calculates a light distribution non-uniformity evaluation value per light source angle of an illumination device on a basis of the chart image signal, and generates compensation data for controlling light distribution non-uniformity from the light distribution non-uniformity evaluation value.

(12)

An endoscopic imaging device including:

an angle control unit configured to control a light source angle with reference to a scope axis of an endoscope; and an imaging unit configured to image a subject in a body cavity during surgery to obtain an image signal, in which information indicating the light source angle and the image signal are output to a control device.

(13)

The endoscopic imaging device according to (12), further including:

a distance information calculation unit, in which distance information to the subject is calculated.

(14)

The endoscopic imaging device according to (13), in which the distance information is calculated from an imaging device condition or the image signal.

(15)

The endoscopic imaging device according to any one of (12) to (14), in which the imaging unit obtains respective image signals of an R signal, a G signal, and a B signal, and the R signal, the G signal, and the B signal are output to the control device.

(16)

The endoscopic imaging device according to any one of (12) to (15), in which
the imaging unit images a predetermined chart, and
the imaged chart image signal is output to the control device.

(17)

A control method including:
controlling image quality of an image for display on a basis of optical axis angle information with reference to a scope axis of an endoscope and an image signal acquired by an image sensor.

(18)

A program for causing a computer to function as a control device including
an image quality control unit configured to control image quality of an image for display on a basis of optical axis angle information with reference to a scope axis of an endoscope and an image signal acquired by an image sensor.

(19)

An endoscopic system including:
an endoscopic imaging device including
a control device including an image quality control unit configured to control image quality of an image for display on a basis of optical axis angle information with reference to a scope axis of an endoscope and an image signal acquired by an image sensor,
an angle control unit configured to control a light source angle with reference to the scope axis of the endoscope, and
an imaging unit configured to image a subject in a body cavity during surgery to obtain an image signal, in which
information indicating the light source angle and the image signal are output to the control device.

REFERENCE SIGNS LIST 1A-1D endoscopic system
10A-10D control device
110A-110D compensation data generation unit
120 angle detection unit
121 aberration detection unit
122 aberration comparison unit
123 aberration database
130A-130D image quality control unit
140 illumination control unit
150A-150C compensation processing unit
2 camera head
21 image sensor
30 illumination device
40 rigid scope
41 lens
50 monitor

The invention claimed is:

1. A control device comprising:
circuitry configured to control image quality of an image for display on a basis of optical axis angle information with reference to a scope axis of a medical camera and an image signal acquired by an image sensor, wherein
the optical axis angle information is information obtained by acquiring light source angle information controlled by an imaging device, wherein the optical axis angle information includes a bent angle relative to an axis perpendicular to the scope axis, the bent angle being either oblique or orthogonal, and
the circuitry is configured to
control image quality of the image for display on a basis of compensation data corresponding to the optical axis angle information and the image signal, and
generate the compensation data on a basis of a chart image signal obtained by imaging a chart positioned according to the optical axis angle information.

2. The control device according to claim 1, wherein
the circuitry is configured to control image quality of the image for display on a basis of distance information indicating a distance to a subject, compensation data corresponding to the optical axis angle information, and the image signal.

3. The control device according to claim 1, wherein
on condition that the image signal has an R signal, a G signal, and a B signal, the circuitry is configured to control image quality of the image for display on a basis of respective image signals.

4. The control device according to claim 1, wherein
the circuitry is configured to control at least one of blur non-uniformity, distortion, or luminance non-uniformity of the image for display.

5. The control device according to claim 1 wherein
the circuitry is configured to
estimate a point spread function that changes depending on a spatial position on a basis of the chart image signal, and
generate compensation data for controlling blur non-uniformity from the point spread function.

6. The control device according to claim 1, wherein
the circuitry is configured to
adjust a light source on a basis of the optical axis angle information by changing a light source angle, and
control image quality of the image for display.

7. The control device according to claim 6, wherein
the circuitry is configured to control light distribution non-uniformity of the image for display.

8. The control device according to claim 1, wherein
the circuitry is configured to
calculate a light distribution non-uniformity evaluation value per light source angle of an illumination device on a basis of the chart image signal, and
generate compensation data for controlling light distribution non-uniformity from the light distribution non-uniformity evaluation value.

9. An endoscopic imaging device comprising:
angle control circuitry configured to control on a light source angle with reference to a scope axis of an endoscope, and
an image sensor to image a subject in a body cavity during surgery to obtain an image signal, wherein
information indicating the light source angle and the image signal are output to image control circuitry configured to control image quality of an image for display on a basis of optical axis angle information with reference to the scope axis and the image signal, wherein
the optical axis angle information is detected based on the information of the light source angle, wherein the optical axis angle information includes a bent angle relative to an axis perpendicular to the scope axis, the bent angle being either oblique or orthogonal, and
the angle control circuitry is configured to
control image quality of the image for display on a basis of compensation data corresponding to the optical axis angle information and the image signal, and generate the compensation data on a basis of a chart image signal obtained by imaging a chart positioned according to the optical axis angle information.

10. The endoscopic imaging device according to claim 9, further comprising:
a distance calculation circuitry configured to calculate distance information to the subject.

11. The endoscopic imaging device according to claim 10, wherein
the distance information is calculated from an imager condition or the image signal.

12. The endoscopic imaging device according to claim 9, wherein
the image sensor obtains respective image signals of an R signal, a G signal, and a B signal, and
the R signal, the G signal, and the B signal are output to the image control circuitry.

13. A control method comprising:
controlling image quality of an image for display on a basis of optical axis angle information with reference to a scope axis of an endoscope and an image signal acquired by an image sensor, wherein
the optical axis angle information is information detected by information obtained by acquiring light source angle information controlled by an imaging device, wherein the optical axis angle information includes a bent angle relative to an axis perpendicular to the scope axis, the bent angle being either oblique or orthogonal,
controlling image quality of the image for display on a basis of compensation data corresponding to the optical axis angle information and the image signal, and
generating the compensation data on a basis of a chart image signal obtained by imaging a chart positioned according to the optical axis angle information.

14. A non-transitory computer readable storage device having computer readable instructions that when executed by circuitry cause the circuitry to:
control image quality of an image for display on a basis of optical axis angle information with reference to a scope axis of an endoscope and an image signal acquired by an image sensor, wherein
the optical axis angle information is information detected by information obtained by acquiring light source angle information controlled by an imaging device,
the optical axis angle information includes a bent angle relative to an axis perpendicular to the scope axis, the bent angle being either oblique or orthogonal,
control image quality of the image for display on a basis of compensation data corresponding to the optical axis angle information and the image signal, and
generate the compensation data on a basis of a chart image signal obtained by imaging a chart positioned according to the optical axis angle information.

15. An endoscopic system comprising:
an endoscopic imaging device including
an image sensor; and
circuitry configured to
control image quality of an image for display on a basis of optical axis angle information with reference to a scope axis of an endoscope and an image signal acquired by the image sensor, wherein
the optical axis angle information is information detected by information obtained by acquiring light source angle information controlled by an imaging device, wherein the optical axis angle information includes a bent angle relative to an axis perpendicular to the scope axis, the bent angle being either oblique or orthogonal,
the circuitry is configured to
control image quality of the image for display on a basis of compensation data corresponding to the optical axis angle information and the image signal, and
generate the compensation data on a basis of a chart image signal obtained by imaging a chart positioned according to the optical axis angle information, and
control a light source angle with reference to the scope axis of the endoscope,
the image sensor to image a subject in a body cavity during surgery to obtain the image signal, wherein
information indicating the light source angle and the image signal are output to the circuitry.

* * * * *